(12) United States Patent
Bongberg et al.

(10) Patent No.: US 12,430,998 B2
(45) Date of Patent: Sep. 30, 2025

(54) DEVICE BASED RESPONDER NETWORK ACTIVATION AND VIRTUAL ASSISTANT INTEGRATION

(71) Applicant: Avive Solutions, Inc., Brisbane, CA (US)

(72) Inventors: Micah R. Bongberg, Kirkland, WA (US); Sameer Jafri, San Diego, CA (US); Rory M. Beyer, San Mateo, CA (US)

(73) Assignee: Avive Solutions, Inc., Brisbane, CA (US)

( * ) Notice: Subject to any disclaimer, the term of this patent is extended or adjusted under 35 U.S.C. 154(b) by 176 days.

(21) Appl. No.: 18/502,371

(22) Filed: Nov. 6, 2023

(65) Prior Publication Data

US 2024/0071197 A1    Feb. 29, 2024

Related U.S. Application Data

(63) Continuation-in-part of application No. 17/100,313, filed on Nov. 20, 2020, now abandoned.

(60) Provisional application No. 62/938,456, filed on Nov. 21, 2019, provisional application No. 63/081,170, filed on Sep. 21, 2020, provisional application No. 63/581,902, filed on Sep. 11, 2023.

(51) Int. Cl.
| | |
|---|---|
| *G08B 21/02* | (2006.01) |
| *G08B 25/00* | (2006.01) |
| *G08B 25/14* | (2006.01) |
| *G08B 27/00* | (2006.01) |
| *H04W 4/16* | (2009.01) |
| *H04W 4/90* | (2018.01) |
| *A61N 1/39* | (2006.01) |
| *H04W 4/02* | (2018.01) |

(52) U.S. Cl.
CPC ............ *G08B 21/02* (2013.01); *G08B 25/006* (2013.01); *G08B 25/14* (2013.01); *G08B 27/001* (2013.01); *H04W 4/16* (2013.01); *H04W 4/90* (2018.02); *A61N 1/3904* (2017.08); *H04W 4/02* (2013.01)

(58) Field of Classification Search
CPC ...... G08B 21/02; G08B 25/006; G08B 25/14; G08B 27/001; H04W 4/90; H04W 4/16; H04W 4/02; A61N 1/3904
See application file for complete search history.

(56) References Cited

U.S. PATENT DOCUMENTS

| | | |
|---|---|---|
| 6,292,687 B1 | 9/2001 | Lowell et al. |
| 6,356,785 B1 | 3/2002 | Snyder et al. |
| 6,493,581 B2 | 12/2002 | Russell |
| 6,658,290 B1 | 12/2003 | Lin et al. |

(Continued)

FOREIGN PATENT DOCUMENTS

| | | |
|---|---|---|
| CN | 105013085 | 11/2015 |
| CN | 108671401 | 10/2018 |

(Continued)

OTHER PUBLICATIONS

International Search Report and Written Opinion dated Feb. 19, 2021 from International Application No. PCT/US20/61482.

*Primary Examiner* — Benyam Haile
(74) *Attorney, Agent, or Firm* — Beyer Law Group LLP

(57) ABSTRACT

A variety of systems, methods, architectures and devices are described that facilitate quicker responses to potential cardiac arrest incidents in a variety of different circumstances.

8 Claims, 8 Drawing Sheets

(56) References Cited

U.S. PATENT DOCUMENTS

| | | |
|---|---|---|
| 6,747,556 B2 | 6/2004 | Medema et al. |
| 6,834,207 B2 | 12/2004 | Miyauchi et al. |
| 6,937,150 B2 | 8/2005 | Medema et al. |
| 6,993,386 B2 | 1/2006 | Lin et al. |
| 7,289,029 B2 | 10/2007 | Medema et al. |
| 8,086,320 B2 | 12/2011 | Saketkhou |
| 8,180,457 B2 | 5/2012 | Matos |
| 8,209,008 B2 | 6/2012 | Hansen et al. |
| 8,565,871 B2 | 10/2013 | Tuysserkani |
| 8,706,225 B2 | 4/2014 | Matos |
| 8,818,522 B2 | 8/2014 | Mass et al. |
| 8,880,168 B2 | 11/2014 | Pearce et al. |
| 8,981,927 B2 | 3/2015 | McSheffrey |
| 9,026,147 B2 | 5/2015 | Galvin et al. |
| 9,035,787 B2 | 5/2015 | Bongberg et al. |
| 9,101,527 B2 | 8/2015 | Madanat |
| 9,232,040 B2 | 1/2016 | Barash et al. |
| 9,289,621 B2 | 3/2016 | Aoyama et al. |
| 9,295,849 B2 | 3/2016 | Elghazzawi et al. |
| 9,307,383 B1 | 4/2016 | Patrick |
| 9,324,120 B2 | 4/2016 | Braun |
| 9,480,852 B2 | 11/2016 | Bonnamy |
| 9,498,152 B2 | 11/2016 | Bowers |
| 9,592,401 B2 | 3/2017 | Freeman et al. |
| 9,619,767 B2 | 4/2017 | Braun |
| 9,628,946 B2 | 4/2017 | Elghazzawi |
| 9,847,030 B2 | 12/2017 | Kadobayashi et al. |
| 9,848,058 B2 | 12/2017 | Johnson et al. |
| 9,872,998 B2 | 1/2018 | Aoyama et al. |
| 9,889,311 B2 | 2/2018 | Horseman et al. |
| 9,897,459 B2 | 2/2018 | Johnson |
| 9,987,193 B2 | 6/2018 | Freeman |
| 10,035,023 B2 | 7/2018 | Das |
| 10,058,469 B2 | 8/2018 | Freeman |
| 10,058,709 B2 | 8/2018 | Tilton, Jr. |
| 10,090,716 B2 | 10/2018 | Stever et al. |
| 10,092,767 B1 | 10/2018 | Newton et al. |
| 10,099,061 B2 | 10/2018 | Buchanan |
| 10,159,848 B2 | 12/2018 | Amann et al. |
| 10,178,534 B2 | 1/2019 | Barash et al. |
| 10,298,072 B2 | 5/2019 | Stever et al. |
| 10,381,118 B2 | 8/2019 | Kellum |
| 10,449,380 B2 | 10/2019 | Andrews |
| 10,504,622 B2 | 12/2019 | Gallopyn et al. |
| 10,543,379 B2 | 1/2020 | Hingston et al. |
| 10,565,845 B1 | 2/2020 | Beyer et al. |
| 10,580,280 B1 | 3/2020 | Picco et al. |
| 10,621,846 B1 | 4/2020 | Beyer et al. |
| 10,638,929 B2 | 5/2020 | Kaib et al. |
| 10,657,796 B2 | 5/2020 | Bowers |
| 10,665,078 B1 | 5/2020 | Picco et al. |
| 10,744,063 B2 | 8/2020 | Freeman |
| 10,773,091 B2 | 9/2020 | Andrews et al. |
| 10,792,506 B2 | 10/2020 | Elghazzawi |
| 10,796,396 B2 | 10/2020 | Braun et al. |
| 10,806,939 B1 | 10/2020 | Malott et al. |
| 10,857,371 B2 | 12/2020 | Gustavson et al. |
| 10,861,310 B2 | 12/2020 | Picco et al. |
| 10,946,209 B2 | 3/2021 | Andrews et al. |
| 10,957,178 B2 | 3/2021 | Beyer et al. |
| 11,077,312 B2 | 8/2021 | Sturman et al. |
| 11,138,855 B2 | 10/2021 | Jafri et al. |
| 2003/0149759 A1 | 8/2003 | Hetherington et al. |
| 2004/0015191 A1 | 1/2004 | Otman et al. |
| 2004/0049233 A1 | 3/2004 | Edwards |
| 2004/0064342 A1 | 4/2004 | Browne et al. |
| 2006/0030891 A1 | 2/2006 | Saltzstein et al. |
| 2006/0041278 A1 | 2/2006 | Cohen et al. |
| 2006/0149321 A1 | 7/2006 | Merry et al. |
| 2006/0149322 A1 | 7/2006 | Merry et al. |
| 2006/0149323 A1 | 7/2006 | Merry et al. |
| 2007/0032830 A1 | 2/2007 | Bowers |
| 2007/0136099 A1 | 6/2007 | Neligh et al. |
| 2007/0162075 A1 | 7/2007 | O'hara |
| 2007/0270909 A1 | 11/2007 | Saketkhou |
| 2007/0299473 A1 | 12/2007 | Matos |
| 2008/0250166 A1 | 10/2008 | Edwards |
| 2009/0070148 A1 | 3/2009 | Skocic |
| 2009/0149894 A1 | 6/2009 | Merry et al. |
| 2009/0284348 A1 | 11/2009 | Anshel Pfeffer |
| 2009/0284378 A1 | 11/2009 | Ferren et al. |
| 2009/0319180 A1 | 12/2009 | Robinson |
| 2010/0017471 A1 | 1/2010 | Brown et al. |
| 2010/0286490 A1 | 11/2010 | Koverzin |
| 2011/0060378 A1 | 3/2011 | Tuysserkani |
| 2011/0071880 A1 | 3/2011 | Spector |
| 2011/0117878 A1 | 5/2011 | Barash et al. |
| 2011/0152702 A1 | 6/2011 | Goto |
| 2012/0087482 A1 | 4/2012 | Alexander, Sr. |
| 2012/0232355 A1 | 9/2012 | Freeman |
| 2012/0271370 A1 | 10/2012 | Hochhalter et al. |
| 2013/0012151 A1 | 1/2013 | Hankins |
| 2013/0065628 A1 | 3/2013 | Pfeffer |
| 2013/0296719 A1 | 11/2013 | Packer et al. |
| 2014/0002241 A1 | 1/2014 | Elghazzawi |
| 2014/0004814 A1 | 1/2014 | Elghazzawi |
| 2014/0031884 A1 | 1/2014 | Elghazzawi |
| 2014/0222096 A1 | 8/2014 | Hu et al. |
| 2014/0222466 A1 | 8/2014 | Kellum |
| 2015/0206408 A1 | 7/2015 | LaLonde et al. |
| 2015/0343229 A1 | 12/2015 | Peterson et al. |
| 2016/0066653 A1 | 3/2016 | Piva et al. |
| 2016/0133160 A1 | 5/2016 | Packer et al. |
| 2016/0140834 A1 | 5/2016 | Tran |
| 2016/0148495 A1 | 5/2016 | Buchanan |
| 2016/0187153 A1 | 6/2016 | Johnson |
| 2016/0210581 A1 | 7/2016 | Braun |
| 2016/0213942 A1 | 7/2016 | Elghazzawi et al. |
| 2016/0296177 A1 | 10/2016 | Gray |
| 2016/0328950 A1 | 11/2016 | Pelletier et al. |
| 2017/0028211 A1 | 2/2017 | Tilton, Jr. |
| 2017/0172424 A1 | 6/2017 | Eggers et al. |
| 2017/0251347 A1 | 8/2017 | Mehta et al. |
| 2017/0281016 A1 | 10/2017 | Elghazzawi |
| 2017/0281461 A1 | 10/2017 | Kokubo et al. |
| 2017/0289350 A1 | 10/2017 | Philibin |
| 2017/0367927 A1 | 12/2017 | Cervantes |
| 2018/0169426 A1 | 6/2018 | Montague et al. |
| 2018/0310159 A1* | 10/2018 | Katz ............... H04M 3/42161 |
| 2018/0369598 A1 | 12/2018 | Newton et al. |
| 2019/0038133 A1 | 2/2019 | Tran |
| 2019/0044362 A1 | 2/2019 | Beyer et al. |
| 2019/0099608 A1 | 4/2019 | Elghazzawi et al. |
| 2019/0117983 A1 | 4/2019 | Andrews et al. |
| 2019/0117984 A1 | 4/2019 | Andrews et al. |
| 2019/0117987 A1 | 4/2019 | Beyer et al. |
| 2019/0117988 A1 | 4/2019 | Beyer et al. |
| 2019/0159009 A1 | 5/2019 | Barash et al. |
| 2019/0168010 A1 | 6/2019 | Elghazzawi |
| 2019/0174289 A1 | 6/2019 | Martin et al. |
| 2019/0279327 A1 | 9/2019 | Braun et al. |
| 2019/0306664 A1 | 10/2019 | Mehta et al. |
| 2019/0318827 A1 | 10/2019 | Chiu et al. |
| 2020/0054885 A1 | 2/2020 | Aprile |
| 2020/0090483 A1 | 3/2020 | Picco et al. |
| 2020/0092700 A1 | 3/2020 | Picco et al. |
| 2020/0206517 A1 | 7/2020 | Martin et al. |
| 2020/0221263 A1 | 7/2020 | Sturman et al. |
| 2020/0242907 A1 | 7/2020 | Beyer et al. |
| 2020/0286352 A1 | 9/2020 | Beyer et al. |
| 2020/0286353 A1 | 9/2020 | Jafri et al. |
| 2020/0373005 A1 | 11/2020 | Halsne et al. |
| 2021/0142639 A1 | 5/2021 | Beyer et al. |
| 2021/0153817 A1 | 5/2021 | Beyer et al. |
| 2021/0154487 A1 | 5/2021 | Bongberg et al. |
| 2021/0228893 A1 | 7/2021 | Akram |
| 2021/0357456 A1 | 11/2021 | Hale et al. |
| 2021/0407273 A1 | 12/2021 | Jafri et al. |
| 2022/0093957 A1 | 3/2022 | Beyer et al. |
| 2022/0359064 A1* | 11/2022 | Pierson ............... G16H 40/40 |
| 2022/0362200 A1 | 11/2022 | Granowitz |
| 2023/0008570 A1 | 1/2023 | Beyer et al. |

(56) References Cited

U.S. PATENT DOCUMENTS

2023/0245544 A1   8/2023   Beyer et al.
2023/0245545 A1   8/2023   Jafri et al.

FOREIGN PATENT DOCUMENTS

| | | |
|---|---|---|
| CN | 111539866 | 8/2020 |
| DE | 202004002106 | 6/2004 |
| EP | 1157717 | 1/2005 |
| EP | 2218478 | 8/2010 |
| EP | 2879759 | 10/2019 |
| JP | 2001/325689 | 11/2001 |
| JP | 2015-58030 | 3/2015 |
| KR | 20160012239 | 2/2016 |
| KR | 101780214 | 10/2017 |
| KR | 102152282 | 9/2020 |
| WO | 2010/66014 | 6/2010 |
| WO | 2018/069383 | 4/2018 |

* cited by examiner

DEVICE BASED RESPONDER NETWORK ACTIVATION AND VIRTUAL ASSISTANT INTEGRATION

CROSS-REFERENCE TO RELATED APPLICATIONS

This application is a continuation-in-part of U.S. application Ser. No. 17/100,313, filed on Nov. 20, 2020 (P020B), which claims priority to U.S. Provisional Application No. 62/938,456, filed on Nov. 21, 2019 and 63/081,170, filed on Sep. 21, 2020. Each of the foregoing applications is incorporated by reference herein in its entirety.

This application also claims priority to U.S. Provisional Application No. 63/581,902, filed on Sep. 11, 2023 (P026P) which is incorporated herein by reference.

FIELD

The present disclosure relates generally to devices, systems and methods that facilitate early detection of potential cardiac arrest incidents and activating responder networks based on the detection of such events. Additionally, the disclosure describes systems, methods and devices for notifying potential responders of nearby emergency medical incidents.

BACKGROUND

Sudden cardiac arrest is one of the leading causes of death. In the United States alone, roughly 350,000 people die each year from sudden cardiac arrest. It is the leading cause of death for individuals over 40 and the #1 killer of student athletes. The most effective treatment for sudden cardiac arrest is the use of CPR coupled with defibrillation. Automated external defibrillators (AEDs) are portable devices designed to automatically check for life-threatening heart rhythms associated with sudden cardiac arrest and to send an electrical shock to the heart to try to restore a normal rhythm when shockable heart rhythms are detected. AEDs are typically designed such that they can be used by a lay person in situations where professional medical personnel are not available.

Given their potential to save lives, automated external defibrillators have been deployed in a relatively wide variety of public and private locations so that they are available in the event that a person in the vicinity goes into cardiac arrest. By way of example, AEDs may be found in corporate and government offices, shopping centers, airports, airplanes, restaurants, casinos, hotels, sports stadiums, schools, fitness centers and a variety of other locations where people may congregate. Although the availability of AEDs has increased over the years, their relatively high cost tends to limit their placement and many locations including schools, sports fields, and a plethora of other places where people congregate don't have an on-site AED available. More concerning, most cardiac arrest incidents occur at home where AEDs are rarely found.

The mortality statistics associated with sudden cardiac arrest are somewhat shocking. Some studies have suggested that 90% of the victims that suffer an out of hospital cardiac arrest (OHCA) die from the incident. That mortality is cut in half when bystander CPR is administered and is cut significantly further when early defibrillation is applied. More generally, statistics show that cardiac arrest survival rates decrease at a rate of on the order of 10% with each passing minute. Thus it is clear that early detection of cardiac arrest incidents and quick responses thereto are critical to increasing cardiac arrest survival rates.

To that end, there have been some efforts to develop community based programs in which volunteer citizen responders who are trained in CPR and AED use, are informed of nearby cardiac incidents. The concept behind the citizen responder projects is that a citizen responder may be able to reach a cardiac incident faster than conventional emergency medical services. These types of programs are sometimes referred to herein as volunteer responder networks (although often, many of the volunteers may be trained personnel including off-duty EMS professionals). Sometimes, such responder networks are tied in with emergency services so that the call for citizen responders can be triggered by an emergency call center operator or dispatcher. Emergency call centers, such as 911 call centers in the United States and Canada, 112 call centers in Europe and 999 call centers in some other jurisdictions, are often referred to as Public Safety Answering Points (PSAPs).

Although these types of systems are clearly beneficial, there are continuing efforts to develop additional and improved techniques that can help shorten cardiac arrest response times and/or otherwise improve cardiac arrest survival rates.

SUMMARY

A variety of systems, methods, architectures and devices are described that can facilitate quicker responses to potential cardiac arrest incidents in a variety of different circumstances.

In one aspect, an intelligent dispatch system is described. The intelligent dispatch system receives an electronic incident message that indicates that a monitoring device has detected a potential cardiac arrest incident. Based at least in part on the received incident message, the system activates a volunteer responder network. In parallel, the system transmits an electronic PSAP incident notification to a public safety answering point (PSAP) that is responsible for medical emergencies occurring in a region that includes the location of the potential cardiac arrest incident. In various embodiments, the volunteer responder network may include a responder network server configured to identify and select a set of one or more responder targets. The responder targets may include at least one of (i) one or more volunteer responders and (ii) one or more connected automated external defibrillators (AEDs) that are deemed nearby the potential cardiac arrest incident. In some embodiments, the responder network server is configured to send electronic nearby incident notifications to the selected set of responder targets requesting volunteer assistance to respond to the potential cardiac arrest incident.

In some embodiments, the intelligent dispatch system maintains an electronic device registry for registered monitoring devices. At least some of the registered monitoring devices have an associated list of contacts to be contacted in the event that the associated registered monitoring device detects a potential cardiac arrest incident. In such embodiments, the system may be further configured to determine whether the monitoring device that detected a potential cardiac arrest has an associated contact list, and if so, transmit a contact incident alert to at least one of the contacts in the associated contact list.

A wide variety of monitoring devices may be integrated into the responder activation system. For example, the monitoring device may be or include a smart watch, a fitness tracker, a fall detector, a smart speaker, a baby monitor, a listening device, a camera, a thermal sensor, a wearable device or any of a variety of other monitors.

The monitors may be configured to detect any of a variety of symptoms indicative of potential cardiac arrest including a victim's ECG, heart rate or blood pressure, agonal breathing, a fall coupled with lack of responsiveness or motion, etc.

Communications between the monitoring device and the intelligent dispatch system may be direct or via one or more intermediate nodes. For example, intermediate nodes may include connected devices located in close proximity to the monitor such as Smartphones, home network hubs, etc. or cloud servers that manage or communicate directly or indirectly with the monitor. The determination that a potential cardiac arrest has been detected may be made by the monitoring device itself, an intermediate node that is independent of the monitoring device, the intelligent dispatch system, or other appropriate nodes based on sensor data from the monitoring device.

In various implementations, the intelligent dispatch system may be an independent node, integrated with or co-hosted with the responder network server, integrated with or co-hosted with a cloud server that manages the monitoring device, or integrated with any other node in the cardiac arrest response network.

In another aspect, a responder network server may be configured to receive an electronic incident message that indicates that a monitoring device has detected a potential cardiac arrest incident potential cardiac arrest incident based on victim parameters detected by a monitoring device. In some embodiments, the server identifies and selects a set of one or more responder targets in response to reception of the incident message. Nearby incident notifications are then sent to the selected set of responder targets requesting volunteer assistance to respond to the potential cardiac arrest incident. The responder targets may include at least one of (i) one or more volunteer responders, and (ii) one or more automated external defibrillators (AEDs).

In another aspect, a responder network server may include an application programming interface (API) that defines a responder network activation call suitable for causing the responder network to activate a responder network. In various embodiments, the responder network call includes various parameters such as (a) an indication of a location of a potential cardiac arrest incident, and (b) at least one of (i) a requestor identifier that identifies the requestor issuing the responder network activation call, and (ii) a monitoring device identifier that identifies a device that detected a patient parameter indicative of the potential cardiac arrest, and (iii) a classifying unit identifier that identifies a device that determined the occurrence of the potential cardiac arrest based at least in part upon sensed data from the monitoring device. A variety of other parameters may be included in the responder network activation call as well.

In yet another aspect, systems and methods for requesting volunteer assistant via a virtual assistant are described. In some embodiments, a virtual assistant server receives a request for volunteer assistance from a volunteer responder network server. The request for volunteer assistance identifies at least one specific target. A nearby incident notification is then sent to be rendered by at least one of a registered virtual assistance enabled device or a virtual assistant enabled device associated with the registered volunteer responder.

In another aspect, an automated external defibrillator (AED) is configured to wirelessly receive an ECG from a wearable ECG monitor that is not a part of the AED. The AED's cardiac rhythm classifier determines whether the received ECG is a shockable rhythm indicative of cardiac arrest. If so, an electronic incident message it transmitted to a remote server to facilitate activating at least one of (i) emergency services, and (ii) a volunteer responder network.

In another aspect various methods of notifying potential volunteer responders of emergency medical incidents detected by monitoring devices are described. In one approach, a determination that a potential medical emergency is made based at least in part on a patient parameter detected by a monitoring device. In response thereto, a volunteer responder network is activated.

In some embodiments, incident notifications are sent to one or more contacts in a contact list associated with the monitoring device. In various embodiments, the determination that the patient parameter is indicative of a potential medical emergency is made by any of: the monitoring device, an intelligent dispatch system, a device network serve, or a Smartphone or other intermediary or computing device in close proximity to the monitoring device that wirelessly receives information indicative of the detected patient parameter from the monitoring device.

In yet another aspect, a defibrillator system includes a communications unit that facilitates communications with external systems. The defibrillator system is configured to wirelessly receive a local incident notification from a monitoring device that is independent of the defibrillator system or an intermediary device in close proximity to such monitoring device. The local incident notification is a notification that was generated based at least in part on a patient parameter detected by the monitoring device that is indicative of a potential cardiac arrest. The defibrillator system generates a nearby incident alert that includes at least one of an audio or visual component. In parallel, the defibrillator system broadcasts a wireless repeated local incident notification suitable for reception by one or more additional devices to facilitate the generation of one or more additional nearby incident alerts by the receiving devices.

In some embodiments, a responder network server or intelligent dispatch system is configured to accept incident notification from, and therefore activate a volunteer responder network in response to, inputs from multiple different types of sources (e.g., 2, 3, 4 or more different types of sources). These may include a variety of different types of monitoring devices, PSAPs, virtual assistants, devices that facilitate user initiated requests for assistance, etc.

In some embodiments, the responder network is configured to send incidents notifications to potential responders via multiple different notification paths as well.

BRIEF DESCRIPTION OF THE DRAWINGS

The invention and the advantages thereof, may best be understood by reference to the following description taken in conjunction with the accompanying drawings in which.

In the drawings, like reference numerals are sometimes used to designate like structural elements. It should also be appreciated that the depictions in the figures are diagrammatic and not to scale.

DETAILED DESCRIPTION

Figure 1:
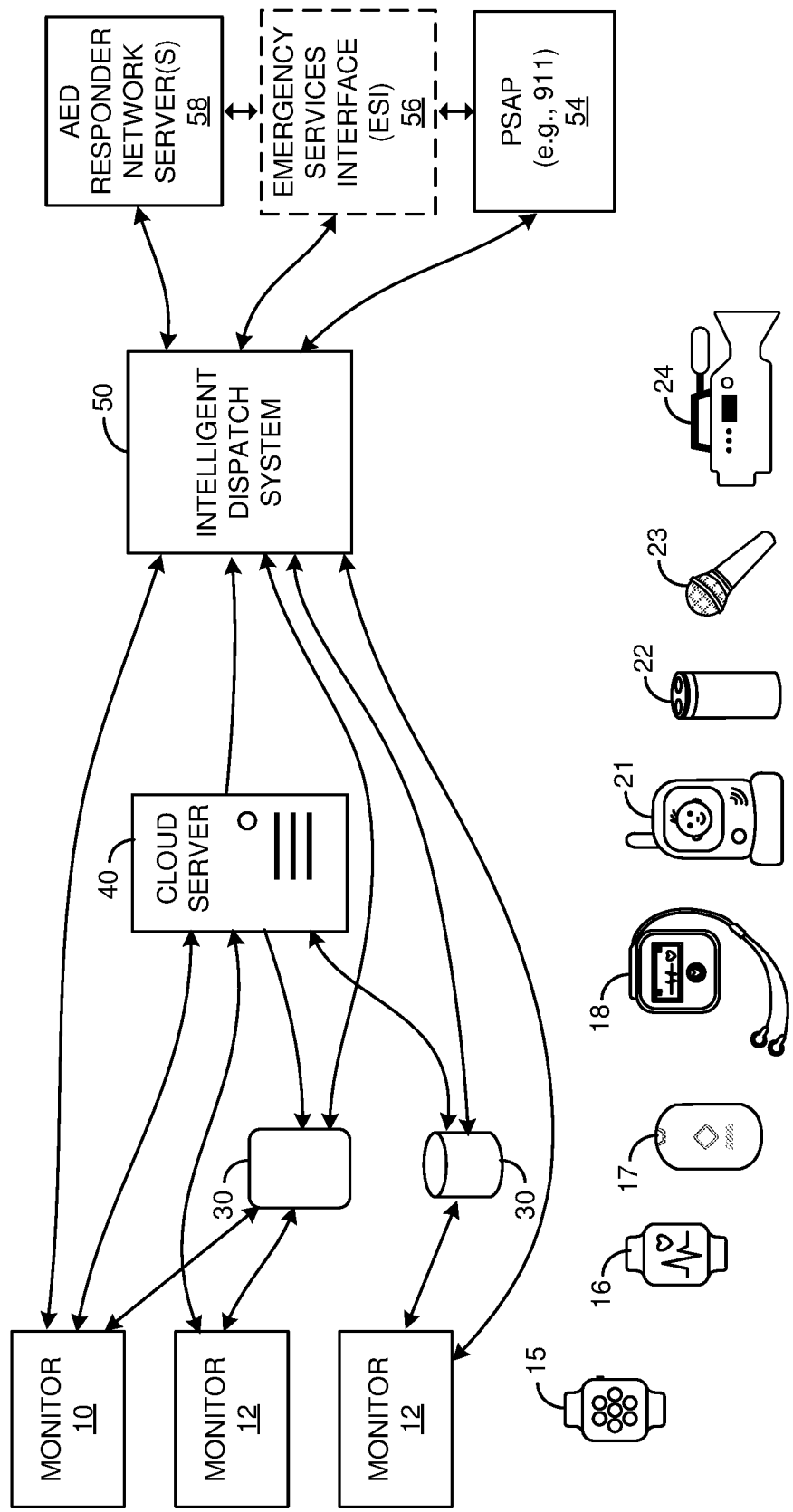
FIG. 1 is a block diagram illustrating components of a cardiac arrest detection and response network in accordance with a described embodiment.

The present disclosure relates generally to early detection of potential cardiac arrest incidents and activating responder networks based on the detection of such events. In another aspect, systems and methods for informing potential responders of a nearby medical incident are described. In another aspect virtual assistant integrations with responder networks and/or AED management functionalities are described.

Sudden cardiac arrest is the abrupt loss of heart function, breathing and consciousness. The condition usually results from an electrical disturbance in the heart that disrupts its pumping action, stopping blood flow to the body. There are a number of symptoms and characteristics that are indicative of sudden cardiac arrest. From a bystander's standpoint, the observation that a victim has, for no apparent reason, collapsed, is unresponsive and is not breathing normally may suggest that the victim may be suffering from sudden cardiac arrest. There are other signs as well. Agonal breathing is a medical term used to describe struggling to breathe or gasping. It is often a symptom of a severe medical emergency, such as stroke or cardiac arrest. The gasping associated with agonal breathing is not true breathing, but rather a brainstem reflex.

As technology has advanced, there are a number of commonly used devices that monitor various aspects of the health, safety and wellbeing of their users and/or have sensors that could be used for such purposes. In some cases, the sensors and processing provided in these types of health monitoring devices (and other common devices) can be modified for use in detecting signs of cardiac arrest. For example, there are currently wearable consumer devices that include built-in heart rate, blood pressure, pulse oximeter, and/or ECG monitors. Such devices include certain smart watches, fitness trackers, health monitors and wearable ECG patches, etc. It is expected that such devices will become even more common as vendors introduce more features to their products. Some of these devices are intelligent devices that can be adapted to analyze the health data (e.g. an ECG) by themselves, whereas others are designed to communicate their data to a nearby Smartphone or other mobile communication device which can analyze their data. Some can communicate directly with remote servers, whereas others require an associated Smartphone, or the like, to facilitate communications with remote servers.

In general, any device that incorporates a heart rate, blood pressure, pulse oximeter or ECG monitor can be adapted to identify signs of a potential cardiac arrest and/or cardiac rhythms indicative of sudden cardiac arrest. These types of devices include: smart watches (e.g., the Apple Watch and others); fitness monitors (e.g. Fitbit activity trackers and others); health or wellness monitors (e.g. Amazon Halo); portable ECG monitors (e.g., AliveCor Kardimobile), wearable ECG patches (e.g., the Vivalink or BardyDx wearable ECG patch, and others); running heart rate bands; insertable or implantable cardiac monitors, etc.

In some applications, a cardiac rhythm classifier that analyzes the ECG may be used to identify when the monitored individual is suffering sudden cardiac arrest. The classifier identifies the occurrence of sudden cardiac arrest by identifying cardiac rhythms indicative of sudden cardiac arrest such as ventricular tachycardia and ventricular fibrillation. By way of example, a cardiac rhythm classifier suitable for identifying sudden cardiac arrest that can readily be incorporated into ECG monitors is described in Applicant's U.S. Pat. No. 11,089,989, (P012) which is incorporated herein by reference. Such a classifier can be incorporated into the monitor itself or into an app or other program executing on a mobile communication device associated with the monitor. Of course, a wide variety of other known or subsequently developed classifiers may be used in other embodiments.

Additionally or alternatively, any heart rate and/or ECG monitoring devices can be used to detect early warning signs of a soon-to-come or potential cardiac arrest incident. For instance, a heart rate monitor can look for abnormal heart pulses or elevated heart rates to detect signs of atrial fibrillation. In a specific example, the Heart Rate app executing on the Apple Watch is currently configured to alert the user of abnormally high or low heart rates and/or irregular heart rhythms. In another specific example, an English company, Tranformative AI has developed an algorithm capable of predicting that a cardiac arrest is going to happen within 5 minutes with a high accuracy. Again, such algorithms can be incorporated into the monitor itself, or into an app or other program executing on a mobile communication device.

Somewhat analogously, there is some evidence that it may be possible to use data from blood pressure monitors and/or pulse oximeters to help identify or predict potential sudden cardiac arrest.

In another example, various devices can be configured to detect agonal breathing, which as described above, is a symptom of sudden cardiac arrest. One way to detect agonal breathing is by analyzing sounds picked up by listening devices. This is possible in part because agonal breathing tends to have a distinctive audio signature. For example, researchers from the University of Washington trained smart devices such as Smartphones and Amazon's Echo to detect agonal breathing based on audio recordings. See, e.g., Contactless Cardiac Arrest Detection Using Smart Devices, by Chan et al. Digital Medicine (2019) 2:52; http://doi.org/10.1038/s41746-019-0128-7.

There are a number of household, consumer and wearable devices that are designed to listen for commands. These include smart speakers, Smartphones, health monitors (e.g. Amazon Halo) and a variety of other devices that are arranged to work in conjunction with virtual assistants (e.g., Amazon's Alexa; Google Assistant, Apple's Siri; Samsung's Bixby, etc.). As will be apparent from the paper referenced above, any of these devices can be adapted to detect agonal breathing. Other devices, such as baby monitors utilize various technologies to monitor a subjects breathing, movement and/or vital signs. Such devices can also be adapted to detect agonal breathing. More generally, any device with an active microphone may potentially be designed to detect agonal breathing.

In yet another example, there are also a number of medical alert devices that incorporate fall detection technology (e.g. pendants, wristbands, clips, etc.). More recently various consumer devices such as watches (e.g., the Apple Watch) have integrated fall detection technology. In some cases, such devices are configured to automatically call one or more of a service provider (e.g. a monitoring service), emergency services (e.g. a PSAP) and/or the user's emergency contacts if and when a fall is detected and the user doesn't indicate that they are OK. As such, wearable devices with fall detection technologies (e.g., watches, bracelets, monitors, pendants, etc.) can be used to identify scenarios in which a wearer of such a device has fallen and appears to be unable to respond—which can also be an indicator of a potential cardiac arrest incident. The sensors most commonly used in fall detection algorithms are accelerometers and gyroscopes. Today, many Smartphones and a wide variety of other consumer devices (wearable or otherwise) include both accelerometers and gyroscopes and as such, can relatively readily be programmed to detect falls and the responsiveness of the wearer after a fall.

In another example, information from a relatively basic pulse or heart rate detection device, a pulse oximeter, or a blood pressure monitor can be paired with information from a fall sensor or the like to identify a potential cardiac arrest incident and trigger an alert. For example, a watch that detects that patient collapsed, paired with detection of really high heart rate or detection of pulseless electrical activity can trigger an alert. In this scenario the watch does not need to be able to sense a full ECG but rather obtains enough information about the wearer's pulse to diagnose the potential cardiac arrest incident and trigger an appropriate alert. Similarly, the detection of a fall coupled with a significant drop in blood pressure may be indicative of a potential cardiac arrest. In general, when cardiac arrest occurs there is little or no blood movement in the arteries and therefore no or very low sensed blood pressure. In some implementations, it may be useful to also monitor the wearer's temperature as a check to verify that the monitor is being worn when a detected "fall" occurs.

In other circumstances room or space monitors may be programmed to identify when a person has fallen within the monitored space. These types of devices may include security systems and other monitoring system and may use a variety of different presence sensing technologies including cameras, thermal sensors, ultrasonics, etc. For example, AI trained processors can be used to analyze video camera, thermal sensor or ultrasonic sensor outputs to detect situations where a person within the camera/sensor's field of view has fallen and appear non-responsive—which again, can be an indicator of a potential cardiac arrest incident. Today, video cameras and other space monitoring sensors are deployed in a wide variety of settings, including the home. These include security cameras, doorbell cams, etc. Some cameras are placed to show rooms inside a house or other building, while others show an entrance or face the street. Thus, the output of security (or other) video cameras can be used to identify falls that occur both inside a house (or other building), or outside on the street, etc. In many implementations a number of cameras are provided which both increases the area monitored and can improve the effectiveness of fall detection. There have also been some efforts to coordinate the output of cameras owned by different entities. One example of this is Amazon's "Neighbors." While such efforts have raised privacy concerns, they do offer the potential of significantly increasing areas in which falls can be automatically detected and therefore can potentially quicken response times in time-sensitive emergencies.

In still other circumstances a patient that is known to have an elevated risk for cardiac arrest, may be prescribed a cardiac monitor for longer term monitoring of the heart's electrical activity thereby facilitating the automatic detection of arrythmias, tachycardia and/or other abnormal heart rhythms. Such monitors include wearable Holter monitors and implantable cardiac monitors (ICM). These cardiac monitors can be particularly useful in detecting and identifying infrequent and/or unexplained heart rhythm abnormalities. Other bioelectronic monitors (wearable, implantable or otherwise) may be arranged to monitor a variety of physiological parameters related to heart function in addition to/or instead of the patient's electrocardiogram (ECG). Implantable monitors have advantages over wearable monitors in that they typically can't be removed by the patient and tend to be best suited for longer term monitoring. Conversely, Holter monitors have significant cost advantages and are particularly well suited for shorter term monitoring—e.g., monitoring over a period of days rather than months. Although cardiac monitors are well suited for identifying abnormal and life-threatening heart rhythms, they do not have the ability to treat life threatening events such as cardiac arrest.

To harness the potential of various devices being used to identify potential medical emergencies, the devices must be capable of communicating the occurrence of an incident in a manner that can generate an effective response. The nature of the appropriate response will vary based on the incident. In some circumstances, the detecting device can generate an audio and/or visual alarm/alert and/or transmit an electronic alert to other appropriate target devices so that people nearby (e.g. family members in the case of an incident in a home) can respond. Alternatively or additionally, the detecting monitoring device can be designed to contact emergency services (e.g., a PSAP) or initiate a process that contacts emergency services so that trained emergency services personnel can promptly respond to the incident. When cardiac arrest is a possibility, it can also be desirable to notify nearby connected AEDs and/or volunteer responders of the incident since in some circumstances, a citizen responder may be able to arrive at the incident with a defibrillator more quickly than professional EMS personnel. Although the potential of using selected commonplace devices to identify potential cardiac arrest incidents is significant, the reality is that there is not currently an infrastructure in place that is well suited for generating a full response to such incidents even if they were detected by a device.

Figure 2:
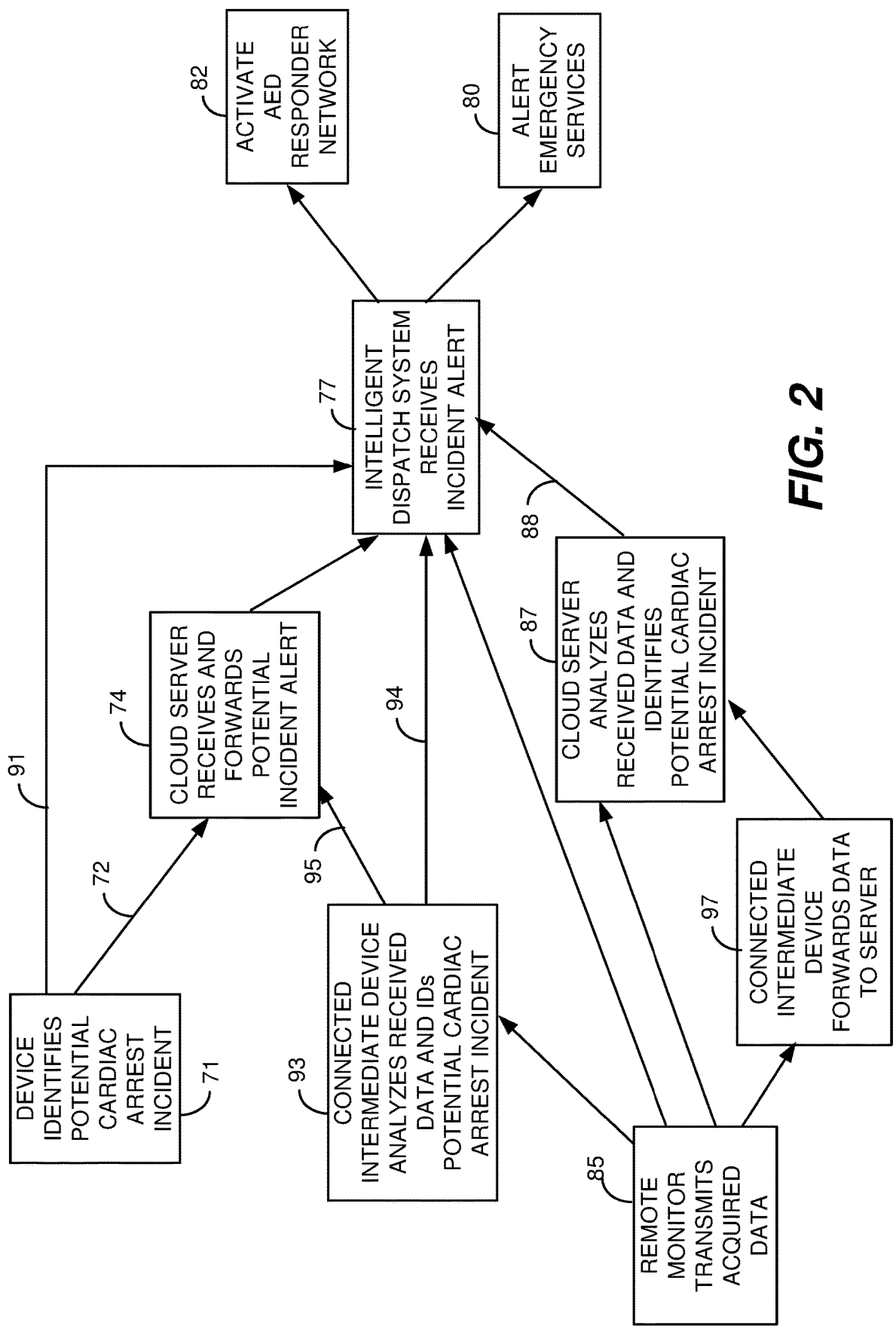
FIG. 2 is a flow chart illustrating a variety of cardiac arrest detection and response activation schemes in accordance with selected described embodiments.

Referring next to FIGS. 1 and 2, a network and various information flows suitable for activating a responder network and/or contacting emergency services based on conditions sensed by various devices will be described. As seen in FIG. 1, the network may include a number of different types of monitors. Some of the monitoring devices 10 are designed to identify a potential sudden cardiac arrest incident based on their own analysis, while other monitoring devices 12 are arranged to forward sensed data to an intermediary device 30 (e.g., Smartphone, base unit, hub, etc.) or a suitable server (e.g., cloud server 40 or intelligent dispatch system 50) that analyzes the data to identify potential sudden cardiac arrest incidents. In some circumstances, when an analyzing device detects what it considers an abnormal rhythm, the abnormal rhythm may be sent to an expert system for more detailed analysis. Such an expert system may be located in a variety of locations, including, for example, at cloud server 40, intelligent dispatch system 50, responder network server 58, a separate system such as a cardiac arrest or health monitoring service (not shown), etc. As suggested above, the nature of the remote monitoring device as well as the triggers used to identify a potential cardiac arrest incident can take a wide variety of forms. For example, the monitors may include both wearable devices (e.g., smart watch 15, fitness tracker 16, fall detector 17, a Holter monitor or other wearable ECG monitor 18, etc.), implantable devices (e.g., implantable cardiac monitors (ICMs) and other implantable biometric monitors (not shown)), and environmental monitoring devices (e.g., baby monitors 21, smart speakers 22, listening devices 23, cameras 24, etc.).

When a potential cardiac arrest incident is detected, a potential cardiac arrest incident message is sent to an intelligent dispatch system 50 which has the ability to both (a) alert emergency services 54 of the incident; and (b) activate an AED responder network 58. Additionally, in some implementations, the intelligent dispatch system 50 (or any other appropriate node in the system such as cloud server 40, intermediary device 30 or a smart device) may be arranged to send incident alerts to one or more contacts in an emergency contact list associated with the detecting device.

In various implementations, the potential cardiac arrest incident message may be sent to the intelligent dispatch system 50 directly from the component that identifies the potential cardiac arrest incident (e.g., a monitor 10, an intermediate device 30 or a cloud server 40) or via one or more intermediaries (e.g., intermediate device 30, cloud server 40, etc.). In various implementations the incident message (and corresponding information) sent to the intelligent dispatch system 50 may be definitive that an emergency response is needed, or may include information (e.g., an ECG segment) that the intelligent dispatch system may use to determine whether an emergency response is needed. The preferred approach for any particular application will vary significantly based on nature of each monitor and its associated network.

In some embodiments, the detecting device (e.g., 10, 12, 15, 16, 17, 18, 21, 22, 23, 24) or an appropriate local intermediate device (e.g., Smartphone or other intermediate device 30) may additionally or alternatively generate a "local" alert—e.g., emit an audio, visual and/or tactile alert and/or send a message to nearby devices that can emit an audio and/or visual alert. Such local alerts can take a variety of different forms and can be useful for both (a) alerting bystanders that are nearby of the incident and (b) reducing the probability of false positives by allowing a user to "cancel" an alert. For example, if a virtual assistant detects agonal breathing, the virtual assistant may trigger a local audio alert such as "I suspect you are having a medical emergency, please respond with 'I'm fine' if you are OK." If/when the person responds with "I'm fine", the event is canceled so that the volunteer responders and emergency services are not sent to the incident. This can help reduce the risk that emergency services and/or the responder network is activated unnecessarily, thereby enhancing trust in the system. Various follow-ups may also be provided—especially when the event is not cancelled. Any of the local alerts can also potentially be heard or seen by people nearby the incident. For example, if an incident occurs in the living room of a home, there may be a family member in another room that is unaware of the incident. That person may hear the local alert generated by the detecting device and can immediately respond to the incident.

Of course, the local alert, as well as the mechanisms used to cancel an alert, may take a wide variety of other forms and the appropriate content and presentation mechanism(s) for the local alert will vary widely based on the nature and capabilities of the detecting device. In some implementations the local alert may be generated in parallel with contacting the intelligent dispatch system or activating the responder network. In others, the local alert may be generated first and the intelligent dispatch system is not informed of the incident, or the responder network is not activated until a reasonable waiting period has passed to give people at the scene the chance to cancel the alert in the event that no emergency exists. In various embodiments, the local alerts may include audio, visual, tactile or other appropriate alerts.

The AED responder network servers 58 may be arranged to send nearby incident notifications to AEDs and/or volunteer responders to inform them of a nearby potential cardiac arrest incident. By way of example, suitable AED inclusive responder networks and emergency services integrations developed by the Applicant are described in U.S. Pat. No. 10,565,845 (P014A), U.S. Pat. No. 10,580,280 (P014B), U.S. Pat. No. 10,957,178 (P014X1) U.S. Pat. No. 11,138,855 (P014X2), U.S. Pat. No. 11,210,919 (P021), U.S. Pat. No. 11,640,755 (P021X1) and U.S. Pat. No. 11,645,899 (P014X3), as well as U.S. Patent Application No. 17/501,900 and 63/581,902 (P026P). All of the foregoing patents and patent applications are incorporated herein by reference.

There are substantial benefits to notifying AEDs and potential volunteer responders of a nearby cardiac arrest incident in parallel with contacting emergency services. This is because even though emergency medical services response times may be good, in many situations, nearby volunteer responders may be able to reach a cardiac incident with a defibrillator faster than conventional emergency medical services. Since early initiation of CPR and defibrillation has been shown to significantly improve victim outcomes in cardiac arrest incidents, early notification of nearby AEDs and volunteer responders through activation of the AED network has the potential of improving the chances of a cardiac arrest victim surviving in circumstances where a volunteer responder is able to arrive at the scene more quickly than professional emergency medical services personnel.

As described in the incorporated responder network patents, a significant advantage of notifying AEDs directly as part of the responder network activation is that the AED can generate an incident alert intended to attract the attention of people in the vicinity of the AED and encourage such individuals to take the AED to the location of an incident. Depending on the circumstances, the people hearing the alert may be trained individuals responsible for the AED (e.g., an administrator) or bystanders that simply happen to be in the vicinity of the AED when the alert happens. Either way, since a person that hears an alert generated by an AED is typically right next to the AED, they may be in the best position to rapidly take the AED to the incident.

The cloud server 40 may take a variety of forms. As will be appreciated by those familiar with remote monitoring devices, many such devices are configured to communicate with a particular server or a set of designated servers for security or functionality related purposes. In many circumstances, the server is associated with a manufacturer, seller and/or service provider. For example, a fitness tracker may be designed to communicate directly or indirectly with a server associated with its seller or manufacturer. Various security systems may be designed to communicate with a designated service provider, etc. Smart speakers and virtual assistants (e.g., Amazon's Alexa; Google Assistant, Apple's Siri; Samsung's Bixby, etc.) are typically configured to communicate with their provider's servers. The communications with the server may be direct (e.g., through a cellular or Wi-Fi connection) or through an intermediary such as an IOT hub, a cell phone, etc.

In such applications the incident message sent to the intelligent dispatch system 50 would typically come from the cloud server 40 regardless of where the message is generated. In applications like virtual assistants in which data is typically sent to a server for analysis, the potential cardiac arrest incident may be identified by processing resources on the cloud server. In other closed system applications, the incident may be identified by processing resources on the monitor, a hub or base unit associated with the monitor and, when appropriate, an incident alert may be sent to the cloud server to be relayed to the intelligent dispatch system.

Alternatively, when a particular monitor 10, or a suitable intermediary 30 has independent general communications abilities, such a device may be configured to send the incident message directly to the intelligent dispatch system 50 when desired.

In some embodiments, the intelligent dispatch system 50 will be implemented on a physical server that is independent of the other servers. In others, the intelligent dispatch system 50 can be incorporated into or integrated with other components such as AED responder network server(s) 58, cloud server(s) 40, an emergency services interface (ESI) 56, servers or computer aided dispatch (CAD) systems associated with EMS dispatch (PSAP) 54 and/or other suitable components.

Referring next to FIG. 2, a few representative alert flows will be described. It should be appreciated that the illustrated flow are exemplary and that a variety of other alert flows may be used as well. In some applications a remote monitoring device 10 itself will determine when a potential cardiac arrest incident has occurred as represented by block 71. Once the remote monitoring device 10 identifies a circumstance indicative of a potential sudden cardiac arrest incident, it sends a potential cardiac arrest incident message (incident alert) to a cloud server 40 with which it communicates, as represented by line 72. The incident alert preferably includes an indication of the location of the incident (e.g., GPS coordinates, address, etc. of the incident). Optionally, the incident message may also include the nature of the diagnosis made by the device and/or at least some of the information that led to the generation of the potential cardiac arrest incident message. For example, if the remote device has an ECG monitor, the incident message may include one or more of an indication that the victim is suffering from cardiac arrest, a diagnosis made by the device (if any, e.g. Ventricular fibrillation), an ECG segment, heart rate, blood pressure, etc.; if the remote device detected agonal breathing, the incident message may include an indication that agonal breathing has been detected, an audio segment from which the diagnosis was made, etc.

In the illustrated embodiment, when the cloud server 40 receives an incident alert, it forwards the alert to an intelligent dispatch system 50 as represented by block 74. The incident alert forwarded by the cloud server 40 may be the same message received from the remote monitoring device 10, or an independent message created by the cloud server based on the incident message received from the remote monitoring unit 10.

When the intelligent dispatch system 50 receives an incident alert (block 77), it both alerts emergency services (e.g., 911) and activates an AED responder network as represented by blocks 80 and 82 respectively. As mentioned above, suitable AED inclusive responder networks and emergency services integrations developed by the Applicant are described in the incorporated responder network patents and patent applications.

FIG. 2 also illustrates other potential alert flow paths. For example, a remote device 12 may not itself do the incident recognition. Rather the remote device may simply acquire data and transmit the acquired data (in raw or processed form) to the cloud server 40 which processes the data as represented by block 85. For example, the Amazon Echo and Echo Dot are smart speakers that also include a microphone. The information picked up by the smart speaker is transmitted to a central server which processes the received audio and provides virtual assistant services (e.g., the Alexa virtual assistant). Many other monitors also utilize this server based analysis architecture. In such embodiments, the cloud server 40 analyzes the received data and itself identifies the potential cardiac arrest incident as represented by block 87. If and when a potential cardiac arrest incident is identified in block 87, the cloud server sends an appropriate incident alert to the intelligent dispatch system 50 as represented by arrow 88 which preferably handles the incident the same way as previously described (blocks 77-82) by notifying emergency services 80 and activating the AED responder network 82 as appropriate.

Several other incident alert flows are also illustrated in FIG. 2. For example, a remote device 10 that identifies a potential cardiac arrest incident may send an incident alert directly to the intelligent dispatch system 50 as represented by arrow 91 or via any applicable intermediate device(s), e.g., hub, base unit, Smartphone etc.

In another example, a remote device 12 that does not itself analyze its sensed information for signs suggestive of a potential sudden cardiac arrest, may transmit some or all of its sensed data (raw or processed) to an intermediate device 30. In some implementations the intermediate device 30 may do the analysis of the sensed data (block 93). If a potential cardiac arrest incident is identified, an incident alert may be sent to either directly to the intelligent dispatch system 50 as represented by arrow 94 or to an associated cloud server 40 as represented by arrow 95. In the later circumstance, the cloud server 40 forwards the incident alert to the intelligent dispatch system 50 as previously described.

In yet another example, a remote device that does not itself analyze it's sensed information for signs suggestive of a potential sudden cardiac arrest, may transmit some or all of its sensed data (raw or processed) to an intermediate device 30, that forwards (block 97) the data to cloud server 40 for analysis. In this circumstance the cloud server analyzes the received data to identify any potential cardiac arrest incident(s). (Block 87).

As discussed above, any of the nodes in the system (e.g., the intelligent dispatch system 50, the cloud server 40, intermediate device 30, or monitoring device 10) may optionally be configured to transmit incident alerts to one or more contacts in an emergency contact list associated with the detecting device (e.g., family, friends, co-workers, etc.). To facilitate such contact alerts, the managing node may include a device registry (e.g. a database) in which monitoring devices may be registered. Any registered device may have an associated contact list that identifies specific individuals and/or devices that should be notified in the event that the associated monitor detects a potential cardiac arrest incident. When a node affiliated with the registry either determines that a potential cardiac arrest has occurred or receives an incident message indicating that a potential cardiac arrest has been detected, the registry is checked to determine whether there is a contact list associated with the detecting monitoring device. If so, the node causes appropriate incident alerts to be sent to the individuals and/or devices identified in the contact list. The inclusion of a device identifier that identifies the detecting monitoring device in the incident messages provides a simple mechanism for identifying the detecting monitoring device and accessing the device registry. The incident notification also preferably identifies the geo-location of the incident so that the contacts know the location of the incident, and if required, can be directed to the scene of the incident.

In some implementations, suitably configured detecting devices (e.g., 10, 12, 15, 16, 17, 18, 21, 22, 23, 24) or appropriate local intermediate devices (e.g., a Smartphone or other intermediate device 30) may additionally or alternatively broadcast an electronic "local incident notification" that indicates that a potential cardiac arrest incident is occurring nearby. For example, a local incident notification can be broadcast using an advertising feature of a short range communication protocol such as Bluetooth or Bluetooth Low Energy (BLE) or any other available notification protocol. Any nearby listening devices that are configured to receive and act upon such notifications then generates a local alert in response to the reception of the local incident notification. Preferably the local incident location identifies the geolocation of the incident so that responders willing to act on the notification can be directed to the incident scene.

A variety of listening devices may be configured to act upon local incident notifications. For example, a public access AED (or a communication unit associated with such an AED) may be configured to respond to such notifications by generating an audio and/or visual alert that may be noticed by people that happen to be nearby the AED—which could be a person associated with the AED (e.g., an owner, administrator or other responsible person), or simply a passerby. A message may be displayed on a screen associated with the AED stating that there is a potential cardiac arrest incident nearby and asking whether the viewer may be willing to help by taking the AED to the scene of the incident. When a person (responder) accepts the incident (e.g., indicates a willingness to help), the responder is directed to the incident. In another example, a volunteer responder may opt-in to receiving local incident notifications on their cell phones or on other suitably enabled devices. Such notifications can be managed by a cell phone operating system, an AED app, a volunteer responder network app, a health app, or any other suitable mechanism.

In some circumstances, selected listening devices (e.g., an AED) may additionally be configured to relay a received local incident notification to extend the range of such notifications beyond the reach of the short range communications protocol used. If/when relaying is used, the relaying would preferably be limited to a small number of hops and/or a geofenced area so that the local incident notifications are only received or acted on by personnel/devices that are deemed "nearby" the incident. Of course, in this context, the definition of "nearby" may be differ based on the needs of any particular application.

It should be apparent that there are several advantages of using local incident notifications. In many circumstances there may be a potential responder nearby when an unwitnessed cardiac arrest incident occurs. Local notifications provide an efficient mechanism for notifying some of the closest potential responders thereby potentially even further quickening response times in some circumstances.

Figure 4:
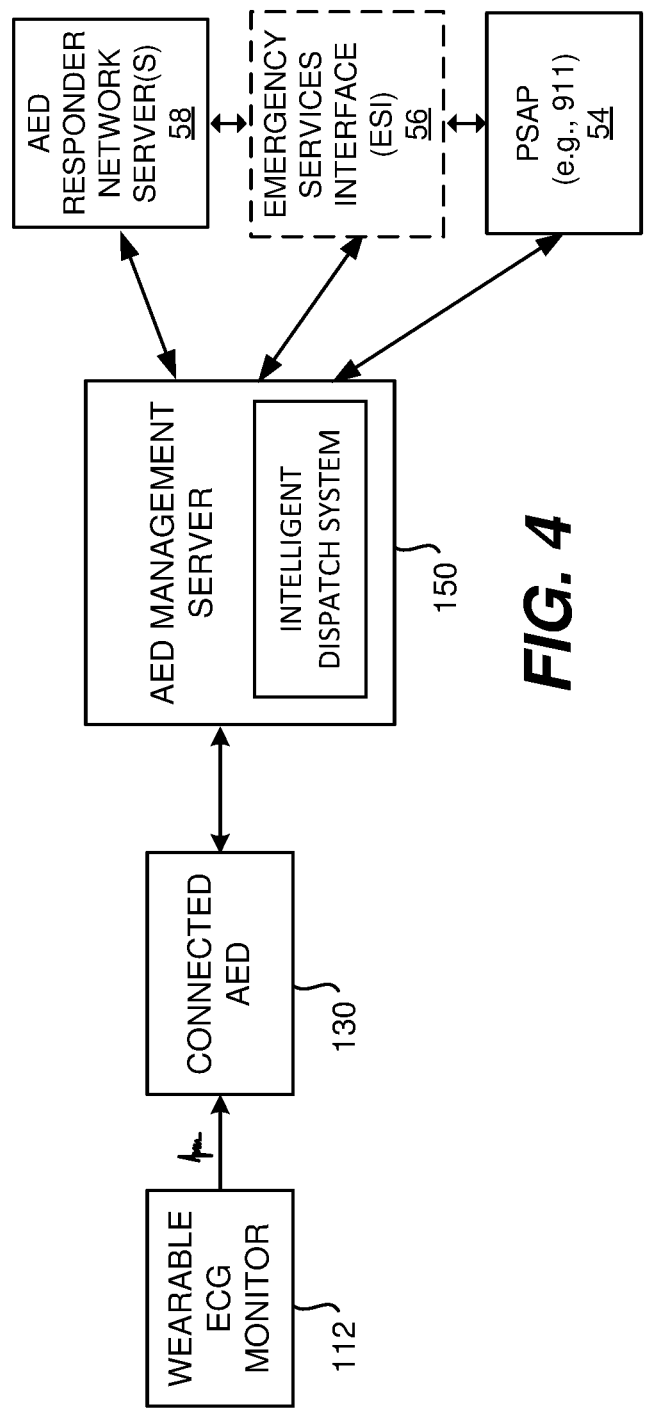
FIG. 4 is a block diagram illustrating components of a cardiac arrest detection and response network in accordance with another embodiment.

Referring next to FIG. 4, another specific implementation will be described. In this embodiment, a wearable device 112 that includes an ECG sensor is configured to send the sensed ECG rhythm to a nearby connected AED 130 for analysis. Such wearable devices may include smart watches 15, fitness trackers 16 and/or other wearable ECG patches or monitors 18 (e.g., the BardyDx or Vivalink ECG patches). The connected AED 130 already includes a cardiac rhythm classifier configured to identify shockable cardiac rhythms. The AED analyzes the received ECG rhythms and determines whether the wearer is suffering from sudden cardiac arrest (i.e., has a shockable heart rhythm). If not, the AED does nothing further. Alternatively, if the AED detects a shockable rhythm it both: (a) emits an audio alert notifying bystanders that the wearer is suffering from cardiac arrest and asking them to initiate CPR and defibrillation using the AED; and (b) sends an electronic incident message to the intelligent dispatch system 50 to thereby alert both emergency services and the AED/volunteer responder network and/or the victim's family and/or friends. The connected AED includes an interface unit or a communications unit suitable for both (a) wirelessly receiving an ECG segment from an ECG monitor, and (b) communicating with the intelligent dispatch system. In many implementations, the ECG segment would be received wirelessly using a short-range communication protocol such as Bluetooth, whereas communications with the intelligent dispatch system would utilize longer range communications protocols such as WiFi or cellular technologies. However, the specific communications technologies used may vary widely based on the respective capabilities of the detecting device and the AED.

The AED is preferably a general purpose automated external defibrillator that is suitable for use by members of the public to treat sudden cardiac arrest and therefore includes a defibrillator controller, high voltage shock delivery capacitor, charging circuitry for charging the capacitor, discharge circuitry and defibrillation electrode pads suitable for placement on a victim to deliver a defibrillation shock, as well as other conventional AED components. By way of example, some of the connected AEDs described in applicant's U.S. Pat. No. 10,773,091 (P006E) and U.S. Pat. No. 10,737,105 (P006A) which are incorporated herein by reference, are highly portable and can readily be adapted for use in this application. The AED may include any of a wide variety of cardiac rhythm classifiers. By way of example, U.S. Pat. No. 11,089,989 (P012), which is incorporated herein by reference describes a suitable cardiac rhythm classifier.

In some implementations, the detecting AED may also broadcast a local incident notification that may be received by nearby listening devices as discussed above. A good example of the usefulness of such local incident notifications is a scenario where a cardiac arrest occurs in a home. A local incident notification broadcast by the detecting AED (or other detecting monitor) may be received by a neighbor who may be both (a) highly motivated to help out; and (b) able to respond quicker than other responder resources.

The described AED intermediary approach may seem unusual because commercially available AEDs are not currently designed to receive ECGs from wearable devices and it is not currently common for people to carry an AED around with them. However, there are a few applications where this type of architecture can be quite beneficial. For example, if a person considers themself at particular risk for sudden cardiac arrest, they may be willing to wear an ECG monitor (which can be as simple as a wearable patch, a smart watch, a fitness tracker or a harness) and carry a small portable connected AED around with them and/or keep such a device nearby. In the event that such a person suffers a cardiac arrest with a knowledgeable bystander nearby (e.g., a family member or friend), the bystander can immediately respond by performing CPR and using the AED. In the event that such a person suffers a cardiac arrest without others around, emergency services and nearby AEDs/volunteer responders can be notified almost immediately of the incident together with its location. As previously discussed, sending alerts to nearby AEDs as part of the AED/volunteer responder network can help increase the pool of potential responders.

Another example is patients that are candidates for implantable cardioverter defibrillators (ICDs). Such patients are often prescribed a wearable defibrillator to wear between the time that they are diagnosed with a need for an ICD and the time that the implant surgery is actually performed (which can be a month or more). Such patients are particularly susceptible to sudden cardiac arrest, which is why a wearable defibrillator is prescribed. Unfortunately, the real world efficacy of wearable defibrillators is remarkably low—with the primary reason for this being that patients find them to be very uncomfortable and stop wearing them—and therefore are not wearing them if and when sudden cardiac arrest occurs. Although actually wearing the wearable defibrillator would be far better from a medical standpoint, if a patient refuses to wear, or stops wearing such a device, the wearable ECG monitor combined with a nearby AED that analyzes the ECG and issues alerts when necessary is far better than the alternative of not monitoring the patient at all.

In yet another example, a baby monitor may include a wearable ECG monitor which can transmit the ECG to an AED for analysis and activating a responder network if/when appropriate.

In the embodiment illustrated in FIG. 4, the connected AED 130 analyzes ECGs detected by the wearable monitor 112. However, in other embodiments, the AED may be configured to identify potential cardiac arrest incidents based at least in part on other information received from a wearable device such as heart rate, blood pressure, blood oxygen level and/or other relevant data.

Figure 6:
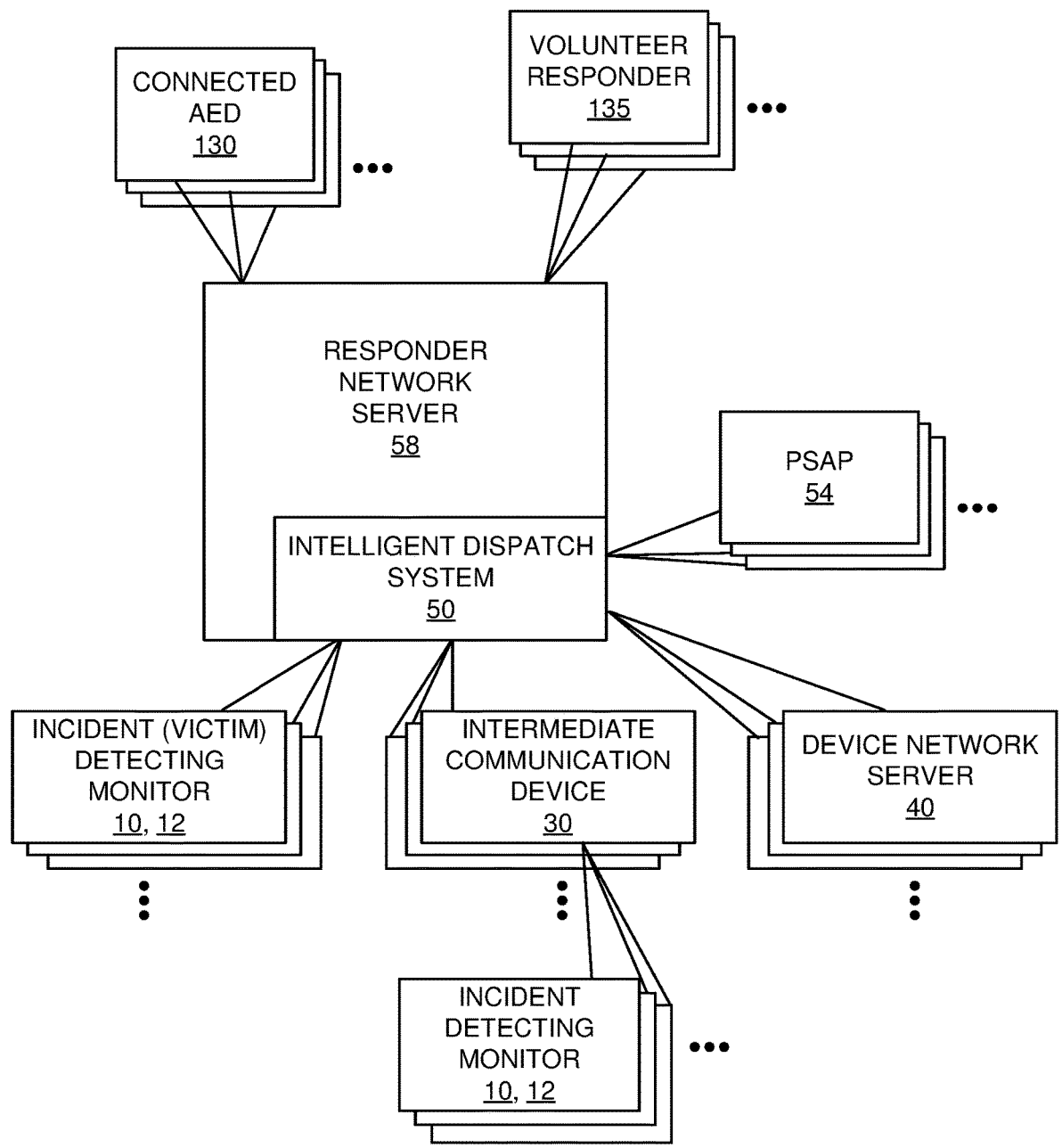
FIG. 6 is a block diagram illustrating a representative network in which an intelligent dispatch system is incorporated into a responder network server.
Figure 7:
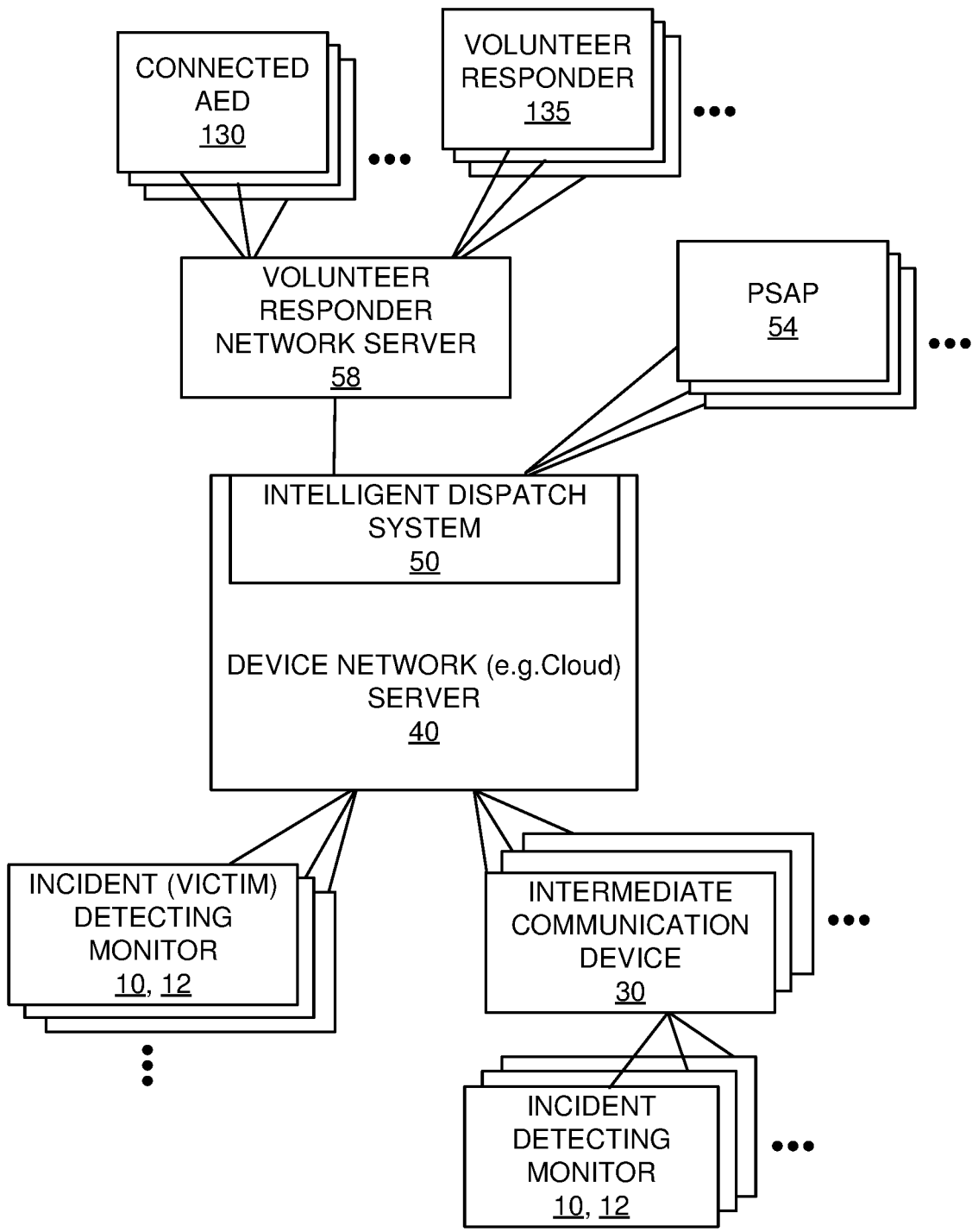
FIG. 7 is a block diagram illustrating a representative network in which an intelligent dispatch system is incorporated into a monitoring device network server or virtual assistant server.

The systems described above include an intelligent dispatch system 50. The intelligent dispatch system 50 can take a number of different forms. In some implementations it may be integrated as a component of the AED Responder Network server (or vice versa). An example of such a system is illustrated in FIG. 6. In other implementations, the intelligent dispatch system 50 may be incorporated into a device network server (e.g., cloud server 40) such as a virtual assistant server or other device management server as illustrated in FIG. 7. In other implementations, intelligent dispatch system 50 may be operated as a separate entity or service and may be arranged to communicate with one or more different AED responder networks. FIG. 1 diagrammatically represents such a system. In still other implementations, the intelligent dispatch system 50 may be integrated with an emergency services interface (ESI) 56 that serves as a data delivery interface for emergency call centers. In still other embodiments, the intelligent dispatch system may be incorporated into an AED management server as illustrated in FIG. 4. The topology of the network will vary somewhat based on the location of the intelligent dispatch system 50, but its basic function may be generally similar regardless of its location.

The interface or integration with an AED responder network is conceptually fairly simple. In general, the intelligent dispatch system 50 will receive an incident alert that indicates at least the nature of the alert (e.g., a potential cardiac arrest incident) and the location of the incident (e.g., GPS coordinates, address, etc.). That information is then forwarded to the AED responder network(s) which utilizes the information along with reported AED status information to identify nearby AEDs and/or volunteer responders to alert of the incident in its normal manner.

The interface with emergency services call centers can be more challenging. Initially, emergency call centers (e.g. 911 call centers) are typically managed locally, and their capabilities vary significantly. Thus, the intelligent dispatch system must initially determine which 911 center to route the message to. Second, while many emergency call centers can receive electronic incident data, many are not arranged to act on incident alerts received only electronically. That is, a voice call is needed in order to initiate a response. Therefore, when the intelligent dispatch service determines that a particular emergency call center can be contacted, it determines the capabilities of that emergency call center and responds accordingly. If the designated emergency call center can initiate a response based on an electronic alert, then the intelligent dispatch system may send an incident alert to the appropriate center in a format suitable for use by the center. Alternatively, if the designated emergency call center requires a phone call to initiate a response, the intelligent dispatch service may initiate a voice call to the appropriate emergency call center. The call may be either a live call from a human operator, or an automated call. Either way, the caller conveys the relevant information to the call center (e.g., the nature and location of the incident, the initiating device/system and any other relevant information).

When the emergency call center has the ability to receive incident information electronically (even if it requires a phone call to initiate a response), the intelligent dispatch system may transmit any electronic information that it has about the incident that would be useful to either the dispatcher or emergency medical services to the call center. This can include information such as the location of the incident and any relevant available information about the incident including any diagnosis made by the detecting or classifying device, e.g., that the victim has fallen and appears non-responsive, that agonal breathing has been detected, that an ECG rhythm indicating sudden cardiac arrest has been detected, etc. When appropriate, the additional information can also include sensed data that might be useful to the emergency responder such as the victim's ECG rhythm, the number of shocks delivered, etc.

Virtual Assistant and Cloud Services Integration

Most of the discussion above focuses on activating a responder network and notifying emergency services based on events detected by devices. In some embodiments, some of these devices, as well as other available devices can be used to notify potential volunteer responders of a nearby incident. As previously mentioned, the incorporated U.S. Pat. No. 10,565,845 (P014A), U.S. Pat. No. 10,580,280 (P014B), U.S. Pat. No. 10,957,178 (P014X1) U.S. Pat. No. 11,138,855 (P014X2), U.S. Pat. No. 11,210,919 (P021), U.S. Pat. No. 11,640,755 (P021X1) and U.S. Pat. No. 11,645,899 (P014X3), as well as U.S. Patent Application Nos. 17/501,900 and 63/581,902 (P026P) describe AED responder networks and emergency services integrations.

Several of those applications focus on sending nearby incident messages to AEDs and/or to volunteer responder's mobile communication devices. Although those are expected to be among the most common volunteer responder notifications mechanisms, it should be appreciated that incident notifications can be sent through various other channels as well, including through the use of various IOT devices.

For example, cloud services and virtual assistants have recently become popular in home applications and elsewhere. Popular virtual assistants include Amazon Alexa; Apple's Siri; Google Assistant; Microsoft's Cortana, Samsung's Bixby and others. Apple's iCloud and similar services from other providers are examples of cloud services. There are also a number of devices such as smart speakers that serve as platforms for integrating virtual assistants and/or cloud services into the home. A few of the popular smart speakers include Amazon's Echo, Apple's Homepod; Google Home and others. Such virtual assistants enabled devices, can provide another pathway for communicating incident alerts to potential volunteers. Specifically, the owner of a smart speaker or any other virtual assistant enabled device can opt-in to receiving nearby incident alerts via such device. This is a particularly low friction mechanism for enrolling participants as volunteers in the responder network. In some systems, such as the Amazon Alexa ecosystem, the opt-in and responder network integration may be implemented as a skill (e.g., an Alexa skill). Such skills make responder network integration particularly easy. Once a device has opted in for notification, the responder network server can include the device (and/or its owner) in the responder network's database of potential volunteer responders.

When integrating with an integrated cloud computing or virtual assistant provider, the system can optionally be configured so that the incident alerts are sent to all, or a designated subset, of the devices associated with a volunteer responder. In the context of something like Apple's iCloud, this could include the responder's phone, tablet(s), Homepod, Apple TV, etc. Of course, Amazon, Google and others have similar integrated networks that can be used to send notifications to multiple devices associated with a volunteer responder.

In some applications, a volunteer responder may identify multiple devices through which they would like to receive incident notifications. This can include the volunteer's mobile communication devices (e.g., phones, tablets, etc.) smart speakers, various virtual assistant enabled devices, any AEDs that the user owns, etc.

Figure 3:
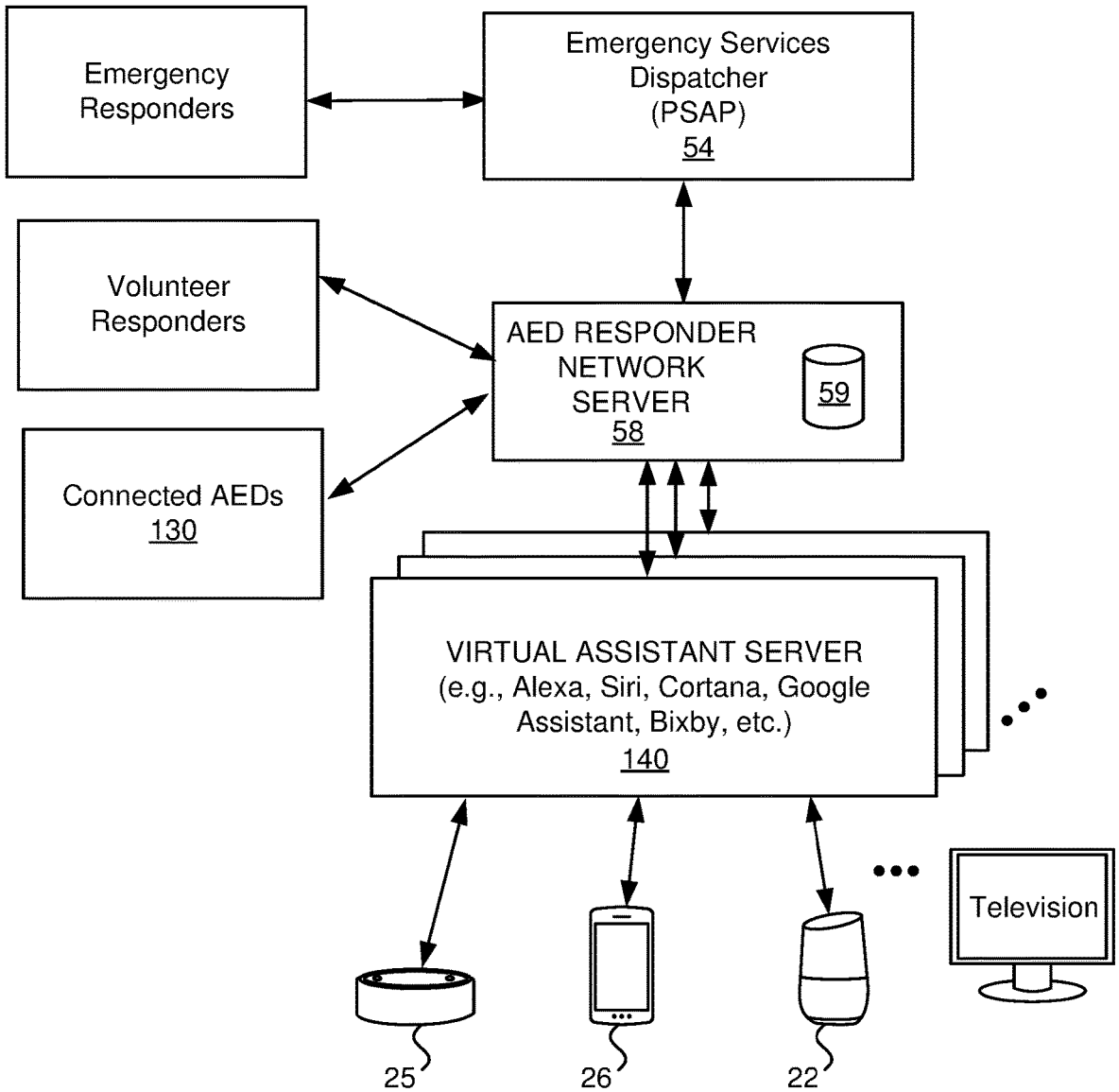
FIG. 3 is a block diagram of a diagram of an architecture for delivering nearby incident alerts via a virtual assistant.

A responder network architecture that supports virtual assistant based notifications is illustrated in FIG. 3. In the embodiment of FIG. 3, the volunteer responder network server 58 is configured to communicate with various PSAPs 54, connected AEDs 130, volunteer responders/volunteer responder devices 132, one or more virtual assistant server systems 140. In some implementations, the responder network server communicates with the PSAPs by way of an optional Emergency Services Interface (ESI) 56 as described in some of the incorporated responder network patents.

Each virtual assistant server system 140 communicates with the virtual assistant enabled devices (e.g., smart speakers 22, home hubs 25, mobile communication devices 26, etc.) in a conventional manner. The responder network server includes a connected AEDs/responder database 59 that identifies the connected AEDs 130, volunteer responders and/or responder devices 132 that have opted in for receiving incident alerts.

The volunteer responder network may be activated in a variety of manners. In some circumstances, the a PSAP sends an incident message to the volunteer responder network server 58 to activate the responder network. In other circumstances, the responder network may be activated directly or indirectly by devices that have detected a potential cardiac arrest as described herein. Of course, the volunteer responder network may be activated in other manners as well.

When the responder network is activated, the responder network server 58 identifies a set of AEDs and/or potential volunteer responders to send a nearby incident message to. The set of volunteer responders includes (but is not limited to) volunteer devices that have opted in to virtual assistant based notifications. The incident alert is then sent to the selected volunteers/devices. In circumstance in which a particular volunteer has elected to receive notifications via multiple paths, the alert may be sent via each of the specified paths, as appropriate. In some circumstances, the notified devices may be filtered based on available location information. For example, if a home device is located near an incident, but a mobile device is quite far from the incident, only the home device may be notified. Of course, the opposite may be implemented as well. For example, if a mobile device is known to be located close to an incident but a home device is not, the incident notification may only be sent to the mobile device. When a device is to be notified through a virtual assistant, the nearby incident message is sent to the associated virtual assistant server system 140 and from there to the designated device(s) (e.g., a smart speaker, smart TV, virtual assistant, etc.), which emits an appropriate audio and/or visual alert (nearby incident alert).

The specific message (wording) used in the nearby incident alert may vary. For example, in some implementations, the listener may be told that there is a nearby cardiac arrest incident that could use a responder to perform CPR and/or use a defibrillator, asked if they can help, and asked to look at their AED or their cell phone to get more details. In other implementations, other selected communications can be sent back and forth between the AED network server and the responder through the virtual assistant in parallel with, or in place of communications through an AED or an AED app. In some implementations, a message sent to the responder may include a link (e.g., a unique URL) which they can access to direct them to the location of the cardiac arrest incident or to dually direct them to the location of an AED and thereafter the incident so that they can pick up a public access AED on the way to the incident.

In some embodiments, the AED and volunteer responder records in the responder network server's database 59 include a field indicating whether the AED's owner/administrator or the volunteer have opted into virtual assistant notifications. If virtual assistant notifications are authorized, the associated record also includes an identification of the network authorized (e.g., Alexa, etc.), as well as the device ID(s) and address(es) to which notifications are to be sent, and any other information required by the network to facilitate sending messages to or from the virtual assistant. In other embodiments, the responder network server may send a query to the virtual assistant server that requests the current location of devices associated with a user. That location information can then be used to determine which device(s) to send incident alerts to.

Nearby incident notifications can also be sent to a variety of other devices that have interfaces suitable for alerting responders. These can include smart watches, fitness trackers, smart speakers and other suitable devices.

When virtual assistants are integrated with AED networks, the virtual assistants can also be used to communicate various AED management related information. For example, an AED management platform may be arranged to notify the owner or administrator of an AED when service or maintenance is required. Such notifications can include messages indicating that it is time to replace the defibrillation electrode pads, that the battery needs replacement or charging, that the system software needs updating or any of a variety of other maintenance related messages. When the AED is a connected device capable of transmitting status check reports to the AED management platform, these messages can be based on real time status checks and can include a variety of other notifications including notification indicating that the defibrillator has been activated or even simply moved from its storage location and give the AEDs current location. Any of these types of messages as well as other management services may be delivered through the virtual assistant. In one simple example, when an AED requires charging, the AED management server sends a message to virtual assistant server 140 that identifies the owner administrator and conveys the AEDs current location and the need to charge the AED. Thereafter, at an appropriate time, the virtual assistance server 140 sends a message to the owner/administrator's device (e.g., smart speakers 22, home hubs 25, mobile communication devices 26, etc.), causing the virtual assistant to inform the owner/administrator of the need to charge the AED and optionally, the AED's current location.

When messages are sent via a virtual assistant, they may be sent to a specific device, or they may be disseminated to a number of devices in parallel. When replacement parts such as electrode pads or a battery are required, the virtual assistant can also provide a mechanism for ordering such parts.

When a smart speaker or other virtual assistant enabled device is used to report a potential cardiac arrest incident and directly or indirectly activate a responder network, the virtual assistant or smart speaker can also report the progress of the responders. E.g., a virtual assistant or smart speaker can inform the initiator that a (or multiple) volunteer responder(s) is on their way and provide periodic updates regarding how far away the closest responder is and/or how long it will take a volunteer responder to arrive.

Although Smart speakers have been highlighted in these terms, it should be apparent that there are a wide variety of other smart devices that support virtual assistants and/or messaging a user can be used for similar purposes. These can include Smart TVs and a variety of other IoT devices, computing devices (e.g. Smartphones, tablet computers, notebook or personal computers, etc.).

Some virtual assistant providers have software development kits that permit outside venders to develop specific skills for their virtual assistant. An example of this is the Alexa Skills Kit. Many of the virtual assistant functionalities described above can be developed using such skills. For example, a responder network notification skill can be created to facilitate notification of volunteer responders of nearby incidents via the virtual assistant. Similarly AED management related notifications can be delivered to AED owners/managers via such skills. Typically, skills that contemplate user notifications would be implemented on an opt-in basis—so that only interested parties would receive such notifications.

PSAP Call Integrations

Figure 5:
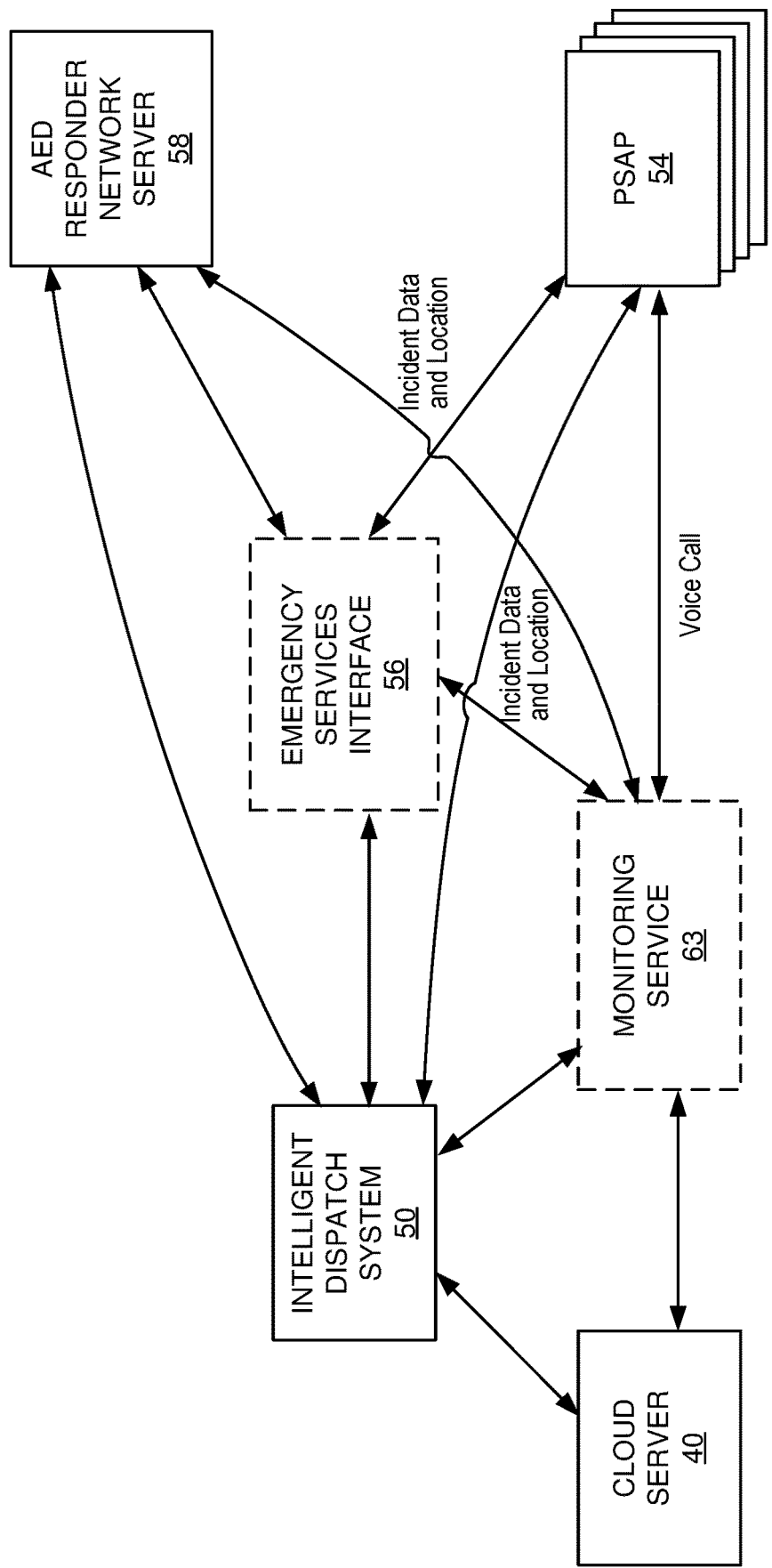
FIG. 5 is a block diagram illustrating various PSAP integrations.

Many of the architectures described above contemplate triggering a call to a PSAP and/or activating a responder network based upon events detected by a device. There are a number of challenges associated with implementing such calls and therefore the frameworks most suitable for implementing the call to emergency services may vary based on the characteristics and requirements of any particular implementation. For example, as diagrammatically illustrated in FIG. 5, one or both of an Emergency Services Interface 56 and a Monitoring Service 63 may optionally be used to help facilitate communications with the PSAP.

By way of background, an inherent risk of device-initiated calls to emergency services is the risk of false positives. That is, detected events that cause a device, server or intermediary node to trigger an alert when no real emergency exits. For example, a virtual assistant can be designed to initiate a call to emergency services if/when a user says something along the lines of "call 911". There are several challenges to implementing such a system in large part due to the risk of false detections. For example, a user could simply be telling a child to call 911 if they see a fire and the virtual assistant logic would need to be robust enough to distinguish such conversation from an actual emergency command to call 911. Because of the risks of unintended (false) calls, some device-initiated calls to emergency services may be routed to a monitoring service (sometimes referred to as a monitoring call center) which is represented by optional block 63 in FIG. 5. The monitoring service 63 typically has human operators that verify that an incident is an actual emergency and if so, initiate a call to the appropriate PSAP.

Monitoring services are utilized in a wide variety of applications where a device (e.g., a fall detector, security alarm, fire alarm, etc.) activates an alarm but does not itself directly contact a PSAP. In many such circumstances, the mechanics of contacting emergency services involves the detecting device sending an alert or alarm (often an Application Programming Interface (API) call) to a designated server. In some circumstances the alert or alarm is sent directly to a server hosted by the monitoring service. In other circumstances a network (cloud) server 40 or management server associated with the device first receives the alert. In such circumstances, the server 40 recognizes the API call from the alerting device as an emergency call and makes an appropriate API call, or sends an appropriate message to the monitoring center 63. Either way, the message would typically include an indication of the geographic location of the alerting device or sufficient information about the alerting device so that the monitoring service can determine the device's location. Upon receipt, the monitoring center attempts to verify whether the API call generated by the alerting device is reflective of an actual emergency. If the incident is verified as an emergency incident, an operator at the monitoring center will typically initiate a voice call directly to the appropriate PSAP—which would typically be the PSAP for the geographic location of the incident.

Depending on the nature of the system, the monitoring center may utilize a variety of different protocols to verify the incident. In some circumstances, the monitoring service may attempt to call or otherwise contact an individual associated with the alerting device to verify that the incident is an actual emergency. In others, the monitoring service may additionally or alternatively review the data that is available to them and attempt to verify the incident is an actual emergency based on such information. In the case of a virtual assistance that received a "call 911" command, this may involve listening to an audio recording of the command and related discussions to provide context that can be used to verify the incident is an actual emergency. In the case of the detection of a fall with no subsequent movement, verification may include a phone call to the person associated with the detecting device to see whether they are responsive and/or OK. Of course, the specific verification protocols used will vary widely based on the originating source that triggered the call and the verification resources that are actually available to the monitoring center.

When a monitoring center verifies a potential cardiac arrest incident, the monitoring center operator may send an incident message to the AED responder network in parallel with their voice call to the appropriate PSAP. This has the advantage of speeding the activation of the volunteer responder network.

In other circumstances there may be a high degree of confidence that an event detected by a device is indeed a true cardiac arrest emergency. For example, if a device (e.g. a heart monitor) detects a cardiac rhythm indicative of cardiac arrest, there is a very high probability that the incident is a true emergency. In such circumstances, the request for assistance may not require verification by a monitoring service. Rather the message from the initiating device may be treated as a verified request that does not require verification before contacting emergency services. In other circumstances, the intelligent dispatch system may automatically or semi-automatically perform any required verification of the incident and/or determine whether involvement of a monitoring center is warranted. When an intelligent dispatch system 50 receives a verified request or verifies the request itself, the intelligent dispatch system 50 will send incident messages to both the AED responder network and the appropriate PSAP. If the intelligent dispatch system 50 determines that a potential incident needs to be verified by a monitoring service, an incident message may be forwarded to the monitoring service 63 for verification. Alternatively, in systems for which verification by a monitoring service is known to be always needed, the monitoring service can be contacted directly by the cloud server 40 or another upstream device as appropriate.

There are a large number of PSAPs and in general, each PSAP is responsible for a designated geographic area. Therefore, in some embodiments, the intelligent dispatch system 50 is configured to determine the appropriate PSAP to transmit any particular incident message to, based on the location of the triggering device. When the triggering device or an intermediary device associated therewith has location services such as GPS (or more generally GNSS), the location may be the geolocation reported by the device. In other circumstances such as a home-based system, the location may be known to the reporting cloud server based on registration or other available information.

In other embodiments, this functionality is provided by an Emergency Services Interface (ESI) 56 is used to both identify the appropriate PSAP and coordinate data communication with the selected PSAP. This is illustrated by optional block 56 in FIG. 5. By way of background PSAPs were originally designed to handle voice calls (e.g., 911 calls), but were not well suited to receive data from external sources that might be relevant to such calls. As the availability of data relevant to emergency incidents increased, Emergency Services Interfaces were developed that helped route data (including, but not limited to device data) that is relevant to a particular incident to the correct PSAP and to provide mechanisms for associating such data with the correct voice call(s) reporting an incident. In general, ESIs have the ability to receive data relevant to an emergency incident, determine the appropriate PSAP to handle that incident, and deliver the relevant data to the appropriate PSAP in a manner than can be utilized by a telecommunicator that is handling a voice call.

Dispatchers within a PSAP will frequently have access to an ESI portal that allows them to receive data relevant to various emergency calls. This may take the form of a separate ESI screen, an ESI frame or window within the computer aided dispatch (CAD) system or in other suitable presentations. In such systems, the dispatcher is able to view data associated with a voice call in the ESI portal. In some circumstances, the ESI serves as a clearinghouse for data supplied to the PSAP. That is, the ESI may take data from one or more distinct sources, process such data appropriately and display the relevant information on the dispatcher's ESI portal.

There are currently several entities that provide emergency services interfaces. In the United States, RapidSOS is currently the largest ESI and is well suited for such applications. One particularly desirable feature of RapidSOS is that they currently have relationships with a large percentage of the emergency call centers in the United States and are already set up to send data received from other sources, including data from other connected devices (not defibrillators) to the call centers. Although RapidS OS is mentioned specifically, it should be appreciated that the same approach can be used with any or with multiple different ESIs as appropriate.

The ESI 56 is configured to communicate with a number of (and potentially a large number of) PSAPs 54. The ESI can use the location data forwarded by the intelligent dispatch system server to determine the appropriate PSAP 54 to handle any particular incident. As discussed above, the PSAP's CAD system or an ESI portal which may be associated with the CAD system is designed to receive data relating to incidents from the ESI 56.

Intelligent Dispatch System APIs

Figure 8:
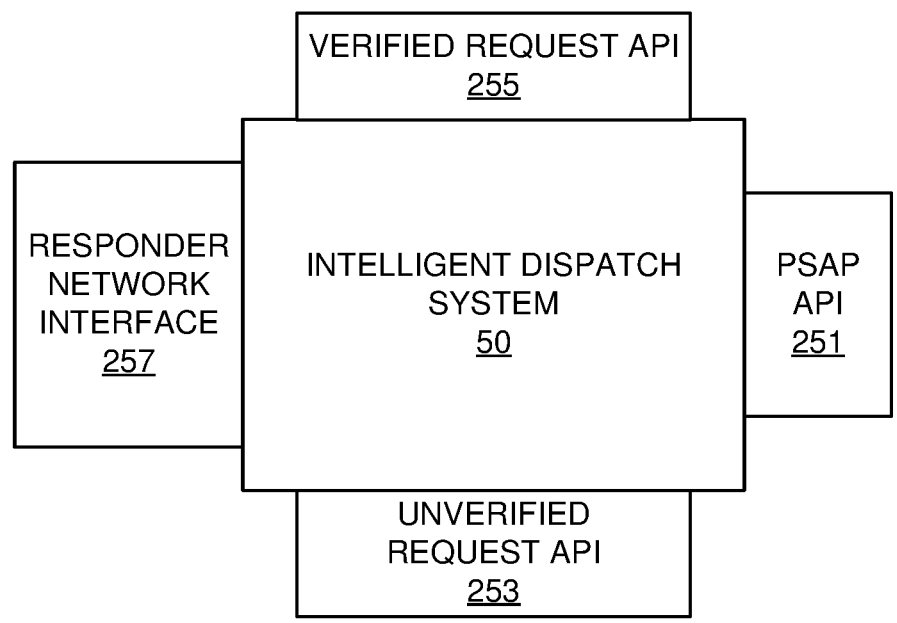
FIG. 8 is a block diagram illustrating selected APIs and interfaces that may be provided to help simplify integration with an intelligent dispatch system.

To facilitate a number of different types of integrations, the Intelligent Dispatch system may include APIs that are suitable for enabling communication with a variety of different types of devices and systems. By way of example, FIG. 8 illustrates a few APIs that may be provided. For example, the intelligent dispatch system may include one or more of a PSAP API, 251, an unverified request API 253, a verified request API 255 and a responder network interface 257. The PSAP API 251 facilitates communications directly or indirectly with PSAPs 54. The responder network interface 257 facilitates communications with responder network server 58. Verified and unverified request APIs 255, 253 facilitate communications with a wide variety of different sources that may send incident messages to the intelligent dispatch system for verified an unverified requests respectfully. In general, incident messages received from a source that does not need to be verified before activating the responder network and/or contacting emergency services may be considered a verified request. Conversely, incident messages that require some level of additional verification before activating the responder network and/or contacting emergency services may be considered unverified requests. In the illustrated embodiment these are shown as separate APIs, although it should be apparent that a single request API can be provided in other embodiments. Explicitly defining intelligent dispatch system APIs simplifies the integration of various monitoring devices, (e.g. any of 10-24), intermediaries (e.g. 30) and networks (e.g. 40) into the responder network ecosystem.

The APIs may define a variety of different calls that may be handled by the intelligent dispatch system, as well as the appropriate formats for such calls and messages sent by the intelligent dispatch system. For example, representative calls may include a responder network activation call and a separate unverified incident reporting call that is used to report incidents that need separate verification. Additionally, it is desirable to define a cancel alert call that causes the intelligent dispatch system to terminate activation of the responder network and the call to emergency services. In many cases it may also be desirable to define the form of various other messages that may separately be received by or sent from the intelligent system to receive or convey other messages and information that may be desirable in the system.

The parameters passed with any call may include one or more predefined parameters. For example, specific parameters passed with a responder network activation call may include (but are not limited to) one or more of the following: (a) a requestor identifier that identifies the unit/system that is actually transmitting the incident request to the intelligent dispatch system (which could be any of a monitoring device 10-24, an intermediary 30 or a network server 40); (b) the requestor's IP address (to facilitate communications with the requester); (c) a device identifier that identifies the specific monitor that detected the potential cardiac arrest incident (this is particularly useful when the detecting device is not the requestor); (d) one or more timestamps associated with the incident—e.g., when the monitoring device first sensed the potential cardiac arrest, when a unit first made the determination that a potential cardiac arrest had occurred, when the requestor transmitted the incident request to the intelligent dispatch system, etc.; (e) an Incident ID—preferably the incident ID is a UUID which may optionally be composed of a concatenation of two or more of the other mentioned parameters such as the device identifier and an incident detection timestamp; (f) a geo-location (e.g., GNSS location) of the incident (which may be a location reported by the monitoring device or an intermediary in close proximity to the monitoring device); (g) when available, location descriptors or other relevant location—for example, if the device is at a fixed location such as a security camera or presence sensor would typically be, the street address and/or other descriptive information such as northwest corner of the $3r$ d floor of an office building, etc.; (h) selected incident information detected by the monitoring device that may be useful to either emergency services or the responder network—(e.g. detected vital signs or symptoms such as an ECG, heart rate or blood pressure, an indication that a fall or agonal breathing was detected, etc.); (i) when available specific patient information—in circumstances in which the monitoring device is associated with a particular person, the monitor or other nodes in the system may have personal or health history related information about the patient that may be helpful to emergency services and/or medical personnel such as patient name, age, gender, medications, known medical conditions, etc.; (j) optionally, one or more identifiers that identify any intermediaries in a transmission path between the detecting monitor and the requestor; (k) an additional information indicator (e.g. a flag that indicates that more information is available or will be coming)—a good example of this is when the monitor senses a victim's vital signs and it is desirable to either stream such information to the intelligent dispatch system or send periodic updates, such information can then be forwarded to appropriate recipients such as responding medical personnel; and (l) a contact list associated with a detecting device. The nature of the contact list can vary widely. For example, if the monitor is a community device, the contact list may be a set of people in the community that should be alerted. Similarly, if the monitor is a personal device, it can be a list of contacts entered by the owner.

When the intelligent dispatch system receives a responder network activation call, it both (a) activates the volunteer responder network; and (b) sends an electronic PSAP incident notification to the appropriate PSAP. In some implementations the intelligent dispatch system itself will determine the appropriate PSAP. In others, the PSAP incident notification may be sent to an emergency services interface 56 which determines the specific PSAP that is responsible for the area in which the incident has occurred and relays/transmits a suitable notification to the appropriate PSAP.

Other Integrations

It should be appreciated that the frameworks described above facilitate a number of devices integrations that provide public health benefits. For example, wearable devices such as a Smart watch can be used to detect that the wearer may be suffering from sudden cardiac arrest (SCA) and initiate a call for help that notifies nearby volunteer responders/devices in addition to emergency services. The watch can record heart rate and/or pulse related information, blood pressure and/or blood oxygen level and transfer such data to a Health app which can be accessed by emergency responders in the event of an emergency incident. Conversely, the Smart watch can serve as a device to which nearby incident alerts may be sent to inform a volunteer responders of nearby incidents for which their help may be useful.

Many Smartphones now include health related apps that seek to provide various fitness and health related functions. Such apps include Apple Health, Google Fit, Samsung Health, Huawei Heath and others. There are a number of integrations that can be made with these types of applications as well. Some heath apps are configured to automatically call emergency services when a potential emergency is detected (e.g., non-responsiveness after a fall). As discussed above, such systems can readily be adapted to trigger a responder network (via intelligent dispatch system 50 or otherwise) in parallel with making a call to emergency services and/or the call to emergency services can be made through the intelligent dispatch system 50 which triggers the responder network in parallel. Conversely, the health-related app can serve as a platform for volunteers receiving nearby incident alerts.

The health app can also serve as a platform for receiving information from, for, or about an AED. For example, an owner/administrator of an AED can elect to receive notifications about the AED's status, maintenance or management through health app. This can include messages informing an owner of the need to replace the AED's electrode pads, charge the AED, physically check the AED, install a software update, etc. It can include notifications that the AED has failed a self-check and needs to be maintained. When replacement parts such as electrode pads or a battery are required, the health app can also provide a mechanism for ordering such parts.

In another example, the health app can include notifications if/when the AED is moved from its storage location or activated etc. which may be indicative of a potential use of the device that the owner/administrator may wish to be informed of.

Applicant has developed an AED that has the ability to broadcast certain information both in emergency and while the AED is in stasis mode. See, e.g., U.S. Pat. No. 11,077,312 (P016B), U.S. Pat. No. 11,452,881 (P016A) and U.S. Pat. No. 11,534,618 (P016BC1), each of which is incorporated herein by reference. In the stasis mode, the broadcast information can include content such as defibrillator status information to be forwarded to a remote AED management server. In an emergency mode, the information can include status information, defibrillator state information that can be used by a receiving device (e.g., the Heath App) to display graphic instructions that correspond to audio instructions provided by the AED, incident data (which may be forwarded to medical personnel), etc. Any or all of these functionalities can readily be incorporated into a more general health app.

Some health apps (e.g., Apple Health) include the concept of a medical ID which stores selected medical information about the owner. Often the medical ID identifies thing such as medications the patient is taking, allergies along with various other patient information. In some implementations, incident information from an AED can be paired with the patient's medical ID or patient record stored in a device associated with the patient to provide a more comprehensive view of the patient. Such information can be transmitted to medical personnel (e.g. an EMT or physician) to give the medical personnel a more comprehensive view of the incident/patient history.

The heath app can also include a map that shows the volunteer responder the location of an incident and optionally directions to the incident, and when appropriate, an AED that can be brought to the incident scene. If desired, the directions can further include location tracking and real time updates based on the responders GPS position. In some embodiments, the map may also include an AED map (or a link to an AED map) that shows the location of nearby defibrillators which increases the accessibility of AED maps since few people actually take the time to download a separate AED map app. In some applications, the health app may also receive incident data from an AED via Bluetooth or other short-range communications protocols. The incident data may be displayed in the health app (e.g., a post incident report) and/or transferred to a management server that forwards the incident data to an electronic patient care reporting (EPCR) system. The health app can also include links to AED training materials that can further enhance public awareness.

Although only a few embodiments of the invention have been described in detail, it should be appreciated that the invention may be implemented in many other forms without departing from the spirit or scope of the invention. Many of the described systems are well suited for in-home applications. This is particularly important because the majority of sudden cardiac arrest incidents occur in the victim's home and many are un-witnessed. Most homes do not have an AED on hand and even if they had an AED they have no mechanism currently for initiating a response if and when an un-witnessed cardiac arrest occurs within the home. The described device-based detection schemes can speed the time to defibrillation by causing an AED to be delivered to the scene when it's needed the most. They also provide a mechanism for beginning the rescue process for un-witnessed SCA (again improving time-to-defibrillation). Although home and un-witnessed SCAs are of particular concern, it should be apparent that the described detection schemes can be helpful in a wide variety of other settings as well.

The use of the described intelligent dispatch system or a responder network server that incorporates the described functionality has a number of advantages. Importantly, it provides an architecture and interfaces which allow the responder network to be activated by a wide variety of different sources. These can include devices, device network servers, PSAPs, intermediate devices in close proximity to monitors and others. In some circumstances it may be desirable to enable witnesses to a cardiac arrest to initiate a request for assistance. A variety of devices can be configured to facilitate such user initiated requests for assistance. For example, any of the described monitors may include an interface (e.g. a button or GUI widget than can be selected by a user) to initiate a request for assistance. Similarly a Smartphone, tablet computer or other mobile communication device may have a health related app or other apps that provide a mechanism for user initiated requests for assistance. Similarly, a virtual assistant can be configured to respond to spoken requests for help. The ability of the responder network server or intelligent dispatch system to integrate with a wide variety of different mechanism that can be used to activate the volunteer responder network (e.g., 2, 3, 4 or more distinct activation mechanism) is believed to be a significant advantage over conventional responder network architectures which are typically configured to be activated in one specific way (e.g. by PSAP dispatchers/ emergency call operators alone, or by users alone).

At the same time, the described architecture and interfaces facilitate nearby incident messages being transmitted to potential responders by a variety of different mechanism, which can help increase the pool of potential responders and reduce volunteer responder response time in some situations. For example, in addition to notifying volunteer responders via traditional mechanism such as sending notifications to the responder's cell phones, nearby incident notifications may be sent via virtual assistants, via connected AEDs, to contacts associated with a detecting device and others. This allows registered responders to received notifications in circumstances in which they might not have otherwise received a notification. It also facilitates alerting nearby bystanders who may be willing to help out and/or interested parties (e.g. registered contacts) to be notified of an incident who might not be registered volunteer responders, thereby expanding the pool of potential responders.

The description above has focused primarily on cardiac arrest, devices for identifying signs indicative of cardiac arrest and mechanisms for activating an AED responder network including volunteers willing to respond to cardiac arrest incidents. However, it should be appreciated that the described approach can be used to identify other types of medical incidents and to activate volunteer responder networks and/or emergency services responses to a variety of other types of medical emergencies. For example, there are a number of situations in which quickly delivering a particular publicly available medication or antidote to a patient can have a significant positive impact on the patient's outcome. One specific example is that an epinephrine injection is often recommended for a patient suffering from a severe allergic reaction (anaphylaxis). Similarly, some public health organizations recommend public administration of Naloxone (or other similar medications) to patients that have suffered an opioid overdose. In both of these situations, the patient or bystanders around the patient may not have immediate access to the required medication, but since these are relatively widely distributed medications, others nearby may have such medications on hand. The described responder network activation approaches can be used to facilitate notifying nearby volunteer responders and/or connected devices (as for example a connected first aid kit or a connected EpiPen) of the nearby incident in the same manner described above with respect to the defibrillator responder network. Similarly, virtual assistants, smart speakers and other paths can be used to notify nearby responders and designated contacts (e.g., family members, coworkers, neighbors, etc.) of such incidents as appropriate as discussed above.

In another example, in certain regions poisonous bites (e.g., snake bites, spider bites, marine creature bites, etc.) are of concern and quickly administering an anti-venom can significantly increase survival chances. In such regions, the responder network can be used to inform nearby volunteer responders and/or connected devices of the need for the anti-venom or antidote.

In yet another example, there has recently been a relatively large grassroots effort referred to as Stop the Bleed which trains the public to stop bleeding. The same responder network activation techniques can be used to notify nearby volunteer responders and/or connected devices of the need for help in responding to these or other types of medical incidents that may be identified by a device.

Of course, there are a wide variety of other situations where there may be a need for a medical instrument, a component of a first aid kit or a medication that at least some volunteer responders may have ready access to and an appropriate responder network would be advantageous. When devices are involved, if the device itself (e.g. a first aid kit, an EpiPen or other medical instrument) is connected then such devices can be integrated in the same manner as the described defibrillators. This can include task specific devices such and a connected EpiPen, or a more generic item such as a connected first aid kit, anti-venom kit, medical supply kit, safety kit etc. that contains or potentially contains the required items.

In some of these types of incidents, the victim may be conscious and able to use a device such as a cell phone, smart speaker, etc. to initiate an emergency alert. In others, a device may automatically detect the incident. In some circumstances a device may take data from a number of sensors and/or consider the victim's location and make a diagnosis based thereon. Therefore, the present embodiments should be considered illustrative and not restrictive and the invention is not to be limited to the details given herein, but may be modified within the scope and equivalents of the appended claims.

The invention claimed is:

1. A method of requesting volunteer assistance to respond to a potential cardiac arrest incident via a virtual assistant server that is configured to communicate with a multiplicity of virtual assistant enabled devices, wherein the virtual assistant server is integrated into an emergency response system that includes a first public safety answering point (PSAP) and a volunteer responder network server that is distinct from and located remotely relative to the first PSAP, wherein the volunteer responder network server is not a PSAP and is configured to, in response to an incident notification received from a first PSAP, identify a plurality of targets including at least a first automated external defibrillator (AED) and at least one selected from a group consisting of volunteer responders and non-AED virtual assistant enabled devices associated with volunteer responders, and wherein the virtual assistant server is not a PSAP and is distinct from and located remotely relative to both the first PSAP and the volunteer responder network server, the method comprising:
at the virtual assistant server, electronically receiving a request for volunteer assistance from a volunteer responder network server that is located remotely relative to the virtual assistant server, wherein the request for volunteer assistance identifies a first target selected from the group consisting of a first registered volunteer responder or a first registered virtual assistant enabled device that is registered with the volunteer responder network server; and
sending a first electronic nearby incident notification from the virtual assistant server to the at least one of the first registered virtual assistance enabled device or a first virtual assistant enabled device associated with the first registered volunteer responder, the first electronic nearby incident notification being configured to cause the at least one of the first registered virtual assistant enabled device or the first virtual assistant enabled device associated with the first registered volunteer responder to render a human perceptible nearby incident alert, wherein the first virtual assistant enabled device or the first virtual assistant enabled device associated with the first registered volunteer responder to which the nearby incident notification is sent is located remotely relative to the virtual assistant server; and
wherein the volunteer responder network server is further arranged to transmit a second electronic nearby incident notification to the first AED via a pathway that does not involve the virtual assistant server.

2. A method as recited in claim 1 wherein the first nearby incident notification includes a link that a recipient may access to direct the recipient to a location of the potential cardiac arrest incident.

3. A method as recited in claim 1 wherein the registration of the first virtual assistant enabled device or the first volunteer responder with the volunteer responder network is implemented using a virtual assistant skill.

4. A method as recited in claim 1 wherein the virtual assistant server further serves as an intermediary in two-way communications between the volunteer responder network server and the first registered virtual assistance enabled device or the first virtual assistant enabled device associated with the registered volunteer responder.

5. A method as recited in claim 1 wherein the first registered virtual assistant enabled device or the first virtual assistant enabled device associated with the registered volunteer responder is a smart speaker and the nearby incident alert is or includes an audio alert.

6. A method as recited in claim 1 wherein the first virtual assistant enabled device or the first virtual assistant enabled device associated with the registered volunteer responder includes a display screen and the nearby incident alert includes a visual message displayed on the display screen.

7. A method as recited in claim 1 wherein the first virtual assistant enabled device or the first virtual assistant enabled device associated with the registered volunteer responder is a health monitor that is not a smartphone or a general-purpose computing device.

8. A method as recited in claim 1 wherein:
the volunteer responder network server is configured to respond to incident notifications received from a multiplicity of PSAPs, including the first PSAP;
the virtual assistant server is configured to communicate with and provide virtual assistant services to a multiplicity of virtual assistant enabled smart speaker devices, including the first virtual assistant enabled device, the virtual assistant enabled smart speaker devices each including a listening function that receives voice commands.

* * * * *